United States Patent
Gu et al.

(10) Patent No.: US 12,428,432 B2
(45) Date of Patent: Sep. 30, 2025

(54) THIENOPYRIMIDINE DERIVATIVES HAVING STEREO CONFIGURATIONS AND USE THEREOF IN MEDICINE

(71) Applicant: SUNSHINE LAKE PHARMA CO., LTD., Guangdong (CN)

(72) Inventors: Zheng Gu, Dongguan (CN); Wanjun Tang, Dongguan (CN); Xinye Yang, Dongguan (CN); Xuli Wang, Dongguan (CN); Weihui Yuan, Dongguan (CN); Yunzeng Cui, Dongguan (CN); Wen Yang, Dongguan (CN); Jianyu Liu, Dongguan (CN); Yingjun Zhang, Guangdong (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 879 days.

(21) Appl. No.: 17/624,572

(22) PCT Filed: Jul. 2, 2019

(86) PCT No.: PCT/CN2019/094307
§ 371 (c)(1),
(2) Date: Jan. 3, 2022

(87) PCT Pub. No.: WO2021/000242
PCT Pub. Date: Jan. 7, 2021

(65) Prior Publication Data
US 2022/0267346 A1  Aug. 25, 2022

(51) Int. Cl.
C07D 495/04  (2006.01)

(52) U.S. Cl.
CPC .................. C07D 495/04 (2013.01)

(58) Field of Classification Search
CPC ...................................... C07D 495/04
See application file for complete search history.

(56) References Cited

U.S. PATENT DOCUMENTS

| | | | |
|---|---|---|---|
| 6,130,223 A | 10/2000 | Jonas et al. |
| 8,969,557 B2 | 3/2015 | Harriman et al. |
| 9,765,089 B2 | 9/2017 | Greenwood et al. |
| 9,988,399 B2 | 6/2018 | Greenwood et al. |
| 10,179,793 B2 | 1/2019 | Ghosh et al. |
| 10,208,044 B2 | 2/2019 | Greenwood et al. |
| 10,472,374 B2 | 11/2019 | Bhat et al. |
| 10,759,812 B2 | 9/2020 | Tang et al. |
| 10,995,099 B2 | 5/2021 | Zhang et al. |
| 11,142,531 B2 | 10/2021 | Lv et al. |
| 11,186,587 B2 | 11/2021 | Wang et al. |
| 2007/0208040 A1 | 9/2007 | Elzein et al. |
| 2017/0166582 A1 | 6/2017 | Ghosh et al. |
| 2017/0166583 A1 | 6/2017 | Ghosh et al. |
| 2017/0166584 A1 | 6/2017 | Ghosh et al. |
| 2017/0166585 A1 | 6/2017 | Bennett et al. |
| 2018/0021341 A1 | 1/2018 | Harriman et al. |

FOREIGN PATENT DOCUMENTS

| | | | | |
|---|---|---|---|---|
| WO | 2015/003881 A1 | 1/2015 | | |
| WO | 2015/007451 A1 | 1/2015 | | |
| WO | 2017/147161 A1 | 8/2017 | | |
| WO | 2018/028721 A1 | 2/2018 | | |
| WO | WO2018133858 | * | 7/2018 | .......... C07D 495/04 |
| WO | 2018/171698 A1 | 9/2018 | | |
| WO | 2018/171699 A1 | 9/2018 | | |
| WO | 2018/228369 A1 | 12/2018 | | |
| WO | 2019/072478 A1 | 4/2019 | | |

OTHER PUBLICATIONS

McMahon et al. (2000).*
Pinedo et al. (2000).*
Vippagunta et al. (2001.*
Banker et al. (1970) Wolff et al. (1995).*
Apr. 1, 2020 Search Report issued in International Patent Application No. PCT/CN2019/094307.
Apr. 1, 2020 Written Opinion issued in International Patent Application No. PCT/CN2019/094307.

* cited by examiner

*Primary Examiner* — Paul V Ward
(74) *Attorney, Agent, or Firm* — Oliff PLC

(57) ABSTRACT

Thienopyrimidine derivative having stereo configurations and use thereof in medicine. Also included are pharmaceutical compositions of the compounds. The compounds or pharmaceutical compositions may be used to inhibit acetyl-CoA carboxylase (ACC). A method for preparing the compounds and the pharmaceutical compositions, and use thereof in treatment or prevention of diseases associated with ACC regulation of mammals, in particular, humans.

13 Claims, No Drawings

THIENOPYRIMIDINE DERIVATIVES HAVING STEREO CONFIGURATIONS AND USE THEREOF IN MEDICINE

CROSS-REFERENCE TO RELATED APPLICATIONS

This is a U.S. national stage application of the International Patent Application No. PCT/CN2019/094307, filed Jul. 2, 2019, which is incorporated herein by reference in its entirety.

FIELD

The present invention relates to thienopyrimidine derivatives with enzyme inhibitory activity and pharmaceutical compositions thereof, and use of the compounds and compositions in the manufacture of a medicament for treating diseases regulated by ACC.

BACKGROUND

Acetyl-CoA carboxylase (ACC) is a rate-limiting enzyme in the first step of fatty acid synthesis and metabolism. In the presence of $Mg^{2+}$, acetyl-CoA carboxylase is carboxylated to form malonyl-CoA with ATP as energy and $HCO_3^-$ as the carboxyl donor. It is a biotin-dependent enzyme.

In humans and other mammals, this enzyme is a tissue-specific enzyme, and it has two subtypes, ACC1 and ACC2, which are different in tissue distribution and function. ACC1 is usually expressed in all tissues, and most expressed in adipogenic tissues (such as liver and adipose tissue), ACC2 is highly expressed in skeletal muscle and heart, and less expressed in liver tissue. ACC1 catalyzes the biosynthesis of long-chain fatty acids. If acetyl-CoA is not carboxylated to form malonyl-CoA, it is metabolized through the Krebs cycle; ACC2 catalyzes the production of Malonyl-CoA on the cytoplasmic surface of mitochondria, and regulates the amount of fatty acids used for β-oxidation by inhibiting carnitine palmityl transferase (CPT-1).

Studies show that ACC inhibitors inhibiting ACC1 can reduce the synthesis of fatty acids, and inhibiting ACC2 can promote the oxidation of fatty acids in the liver, thereby reducing the accumulation of lipids in the body. It can effectively treat diseases related to obesity, hypertension, diabetes, tumors, dyslipidemia, and hyperlipidemia, and type II diabetes, non-alcoholic fatty liver disease (NAFLD) and non-alcoholic steatohepatitis (NASH) caused by the accumulation of lipids in the liver that cause insulin resistance in the liver.

Non-alcoholic steatohepatitis (NASH) is a chronic progressive liver disease caused by the accumulation of fat in the liver, which can lead to cirrhosis, liver failure and hepatocellular carcinoma. There are many reasons for NASH, such as age, obesity, Body Mass Index (BMI), insulin sensitivity, dyslipidemia, hypertension, and abnormal activity of liver function-related enzymes (such as alanine aminotransferase (ALT) or aspartate aminotransferase (AST)), etc. According to reports, patients with metabolic syndrome (mainly central obesity, hypertension, insulin resistance, high triglycerides and low high density lipoprotein) are positively associated with the risk of NASH. In patients with diabetes or obesity older than 50 years, 66% of liver biopsies revealed that NASH was accompanied by severe fibrosis. In the United States, about 12% of people are deeply affected by this disease, and the proportion will rise to 22% in people with diabetes. What is more noteworthy is that about 15-25% of patients with NASH will develop cirrhosis, which is another cause of liver cancer after viral hepatitis and alcoholic hepatitis. Cirrhosis is the main cause of death due to liver disease, which directly leads to liver decompensation and a mortality rate of nearly 4% per year.

Patent application WO201307116 discloses a series of thienopyrimidine derivatives, wherein the compound GS-0976 (firsocostat) disclosed in Example I-181 is currently the most promising drug for such diseases in clinical practice.

The racemate A13 of the compound described in this application is disclosed in the patent application WO2018133858 (Example 13).

For the treatment of obesity, hypertension, diabetes, and dyslipidemia, people still need other alternative therapies, and for NASH, the current treatment methods are limited.

SUMMARY OF THE INVENTION

The present invention relates to a compound as an Acetyl-CoA carboxylase (ACC) inhibitor, and a pharmaceutical composition comprising such an inhibitor. The present invention further relates to use of the compound or the pharmaceutical composition thereof in the manufacture of a medicament, and the medicament can treat diseases and/or disorders by inhibiting ACC activity with the compound. The present invention further provides a synthesis method of the compound. The compound provided herein show excellent biological activity and pharmacokinetic properties.

In the present invention, the inhibition of ACC refers to the inhibition of only ACC1, only ACC2, or both ACC1 and ACC2. Inhibition of any ACC subtype should beneficially affect abnormalities associated with metabolic syndrome. Preferably, the ACC inhibitor should inhibit the two isoenzymes of this type of enzyme.

Specifically:

In one aspect, the present invention provides a compound having Formula (I) or an N-oxide, a hydrate, a solvate, a metabolite, a pharmaceutically acceptable salt or a prodrug thereof,

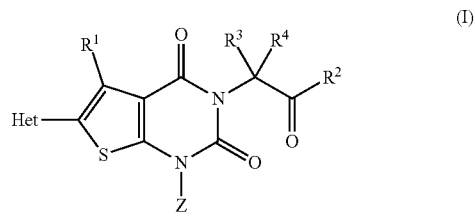

(I)

wherein:

Z has the following structures:

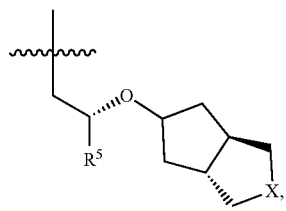

-continued

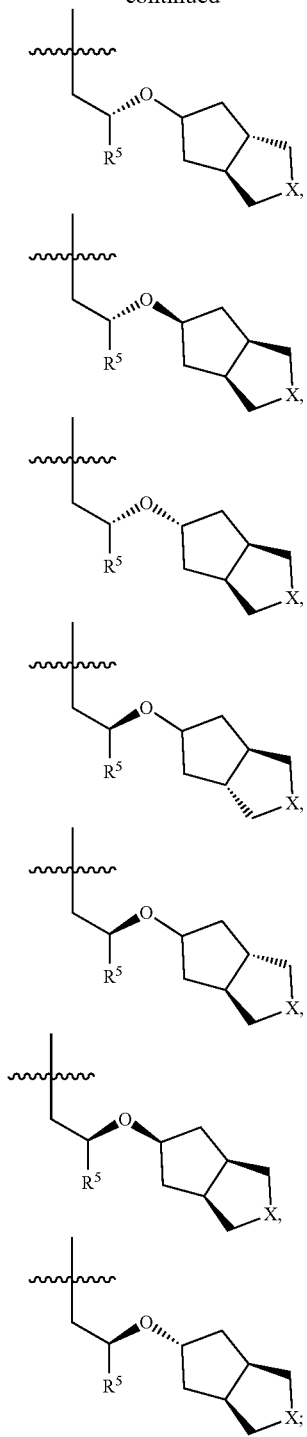

Het is 3-10 membered heterocyclyl or 5-10 membered heteroaryl, the 3-10 membered heterocyclyl and 5-10 membered heteroaryl can be optionally substituted by 1, 2, 3 or 4 substituents independently selected from H, D, oxo (=O), F, Cl, Br, I, hydroxyl, amino, nitro, cyano, $C_{1-6}$ alkyl, $C_{1-6}$ alkoxy, $C_{1-6}$ haloalkyl and carboxyl;

$R^1$ is H, D, F, Cl, Br, I, hydroxyl, amino, nitro, cyano, $C_{1-6}$ alkyl, $C_{1-6}$ alkoxy or $C_{1-6}$ haloalkyl;

$R^2$ is —OR or —NR$^a$R$^b$;

each $R^3$ and $R^4$ is independently H, D, $C_{1-6}$ alkyl, $C_{1-6}$ hydroxyalkyl or $C_{1-6}$ haloalkyl;

each $R^5$ is independently $C_{6-10}$ aryl or 5-10 membered heteroaryl, the $C_{6-10}$ aryl and 5-10 membered heteroaryl can be optionally substituted by 1, 2 or 3 $R^6$; wherein, each $R^6$ is independently H, D, F, Cl, Br, I, hydroxyl, amino, nitro, cyano, $C_{1-6}$ alkyl, $C_{1-6}$ alkoxy, $C_{1-6}$ haloalkyl, $C_{1-6}$ haloalkoxy, $C_{1-6}$ cyanoalkyl or $C_{1-6}$ hydroxyalkyl;

each X is independently O or NR$^7$;

each $R^7$ is independently H, D, F, Cl, Br, I, hydroxyl, amino, nitro, cyano, —C(=O)OH, —SO$_2$R$^c$, $C_{1-6}$ alkyl, $C_{3-6}$ cycloalkyl, $C_{1-6}$ alkoxy, $C_{1-6}$ haloalkoxy, $C_{1-6}$ alkylamino, $C_{1-6}$ haloalkyl, $C_{1-6}$ cyanoalkyl or $C_{1-6}$ hydroxyalkyl;

each R, R$^a$, R$^b$ and R$^c$ is independently H, D, $C_{1-6}$ alkyl, $C_{1-6}$ alkoxy, $C_{3-6}$ cycloalkyl or $C_{1-6}$ haloalkyl;

or, R$^a$ and R$^b$, together with the N atom to which they are attached, form 4-6 membered heterocyclyl, and the 4-6 membered heterocyclyl can be optionally substituted by 1, 2, 3 or 4 substituents independently selected from oxo (=O), D, F, Cl, Br, I, hydroxy, amino, nitro, cyano, $C_{1-3}$ alkyl $C_{1-3}$ alkoxy and $C_{1-3}$ haloalkyl.

In some embodiments, the X is O, NH or N—SO$_2$R$^c$; R$^c$ is H, D, methyl, ethyl, isopropyl, methoxy or ethoxy.

In some embodiments, the Het is

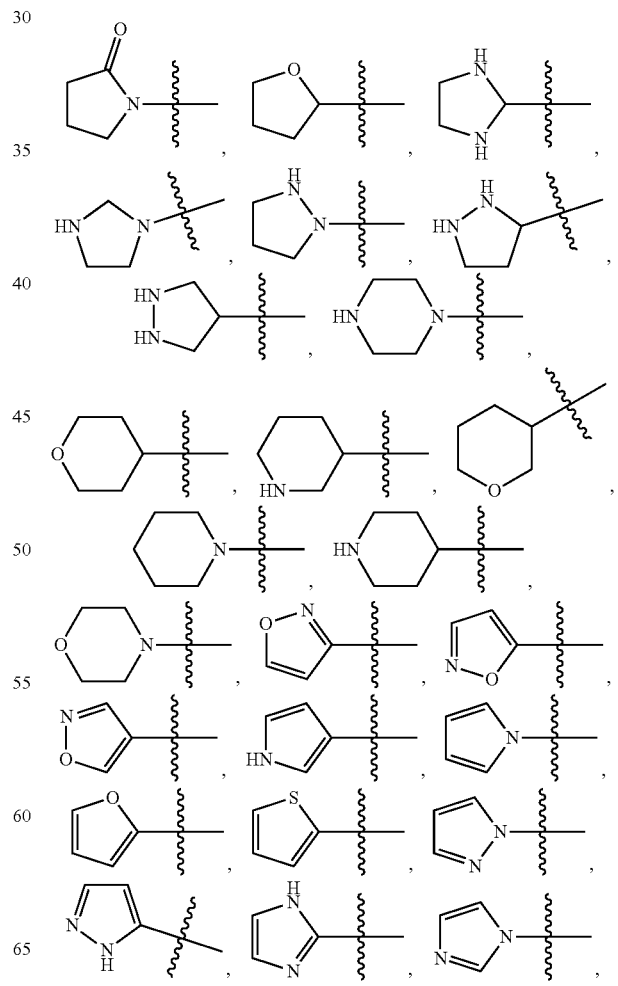

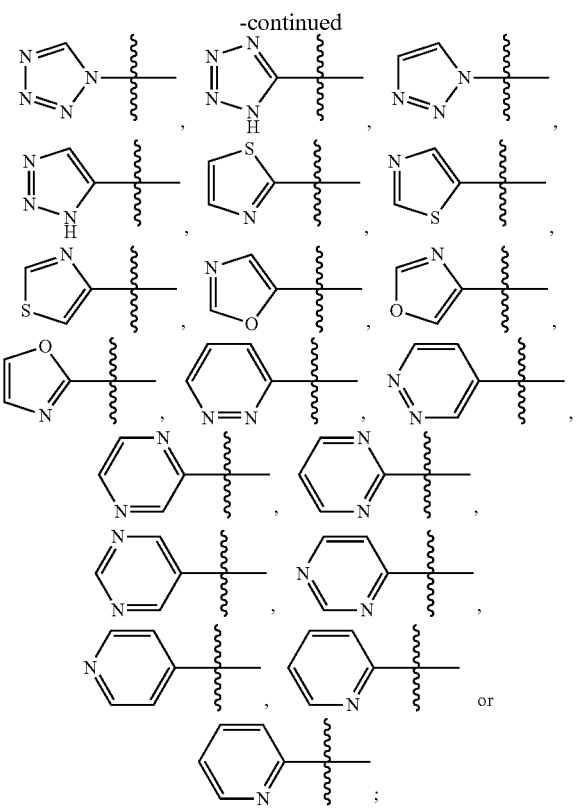

wherein, the Het can be optionally substituted by 1, 2, 3 or 4 substituents independently selected from H, D, oxo (=O), F, Cl, Br, I, hydroxyl, amino, nitro, cyano, methyl, ethyl, isopropyl, methoxy, ethoxy, isopropyloxy, trifluoromethyl, difluoromethyl and carboxyl.

In some embodiments, the $R^1$ is H, D, F, Cl, Br, I, hydroxyl, amino, nitro, cyano, methyl, ethyl, methoxy, ethoxy, isopropyloxy or trifluoromethyl.

In some embodiments, the $R^2$ is —OR or —NR$^a$R$^b$; each R, R$^a$ and R$^b$ is independently H, D, methyl, ethyl, methoxy, ethoxy, cyclopropyl, cyclobutyl, cyclopentyl or cyclohexyl; or, R$^a$ and R$^b$, together with the N atom to which they are attached, form 4-6 membered heterocyclyl, and the 4-6 membered heterocyclyl is selected from:

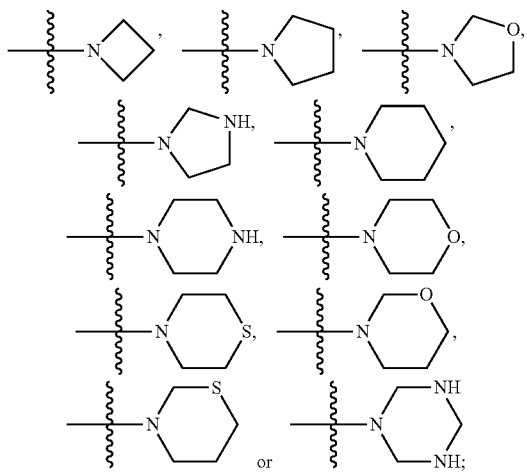

the 4-6 membered heterocyclyl can be optionally substituted by 1, 2, 3 or 4 substituents independently selected from oxo (=O), D, F, Cl, Br, I, hydroxyl, amino, nitro, cyano, methyl, ethyl, isopropyl, methoxy, ethoxy, trifluoromethyl and difluoromethyl.

In some embodiments, each $R^3$ and $R^4$ is independently H, D, methyl, ethyl, n-propyl, hydroxymethyl, difluoromethyl, trifluoromethyl or 2-hydroxyethyl.

In some embodiments, each $R^5$ is independently phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl; wherein the phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl and pyridazinyl can be optionally substituted by 1, 2 or 3 $R^6$; wherein each $R^6$ is independently H, D, F, Cl, Br, I, hydroxyl, amino, nitro, cyano, methyl, ethyl, n-propyl, isopropyl, methoxy, ethoxy, trifluoromethyl, difluoromethyl, trifluoromethoxy, difluoromethoxy, hydroxymethyl or 2-hydroxyethyl.

In some embodiments, the compound provided herein has one of the following structures:

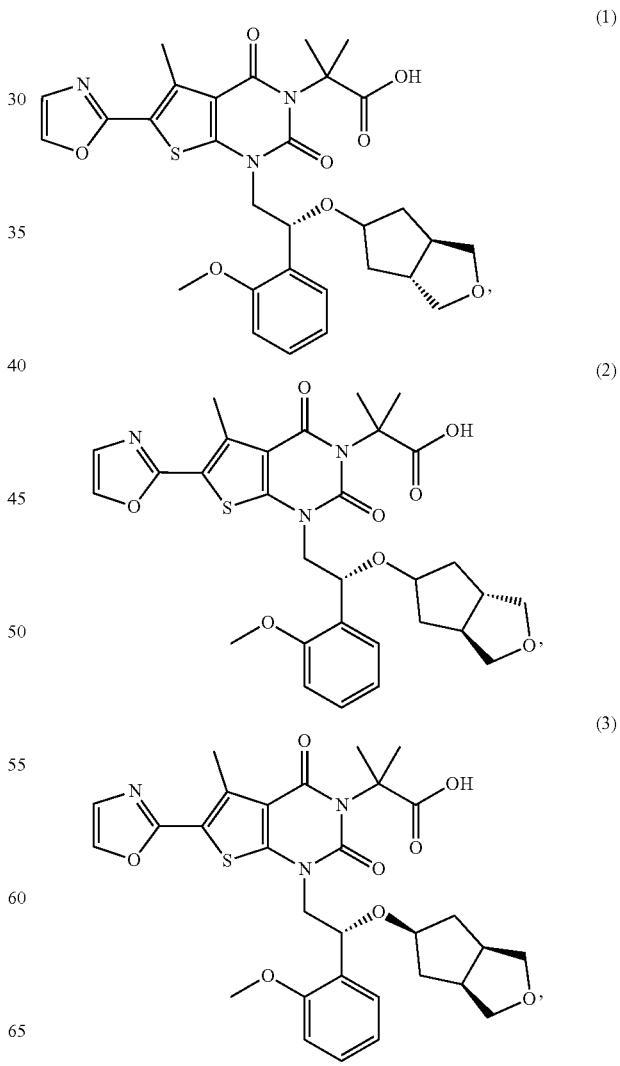

(4)

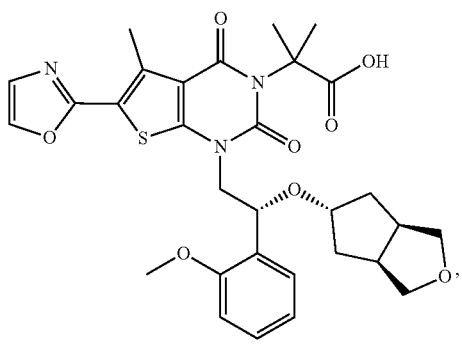

(5)

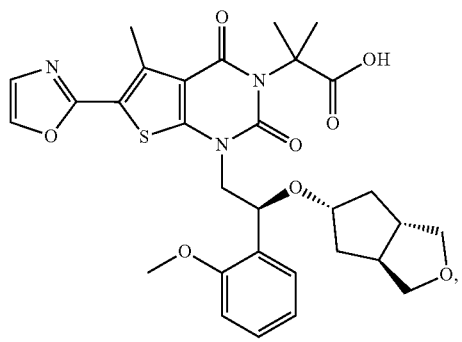

(6)

(7)

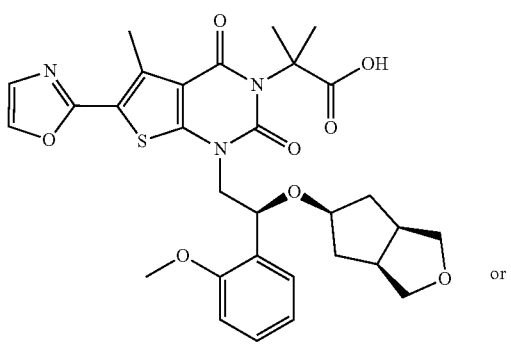

or (8)

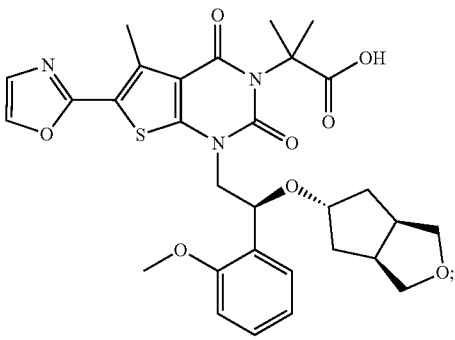

or an N-oxide, a hydrate, a solvate, a metabolite, a pharmaceutically acceptable salt or a prodrug thereof.

In other aspect, provided herein is a pharmaceutical composition comprising a compound having Formula (I) disclosed herein or an N-oxide, a hydrate, a solvate, a metabolite, a pharmaceutically acceptable salt or a prodrug thereof, and a pharmaceutically acceptable carrier, an excipient, a diluent, an adjuvant, a vehicle or a combination thereof.

In one aspect, provided herein is use of the compound having Formula (I) or a pharmaceutical composition thereof in the manufacture of a medicament for preventing, managing, treating or lessening diseases regulated by ACC.

In some embodiments, the diseases regulated by ACC of the present invention are metabolic disorders and tumor disorders.

In other embodiments, the diseases regulated by ACC of the present invention comprise metabolic disorders and tumor disorders, and the metabolic disorders comprise insulin resistance, obesity, dyslipidemia, metabolic syndrome, type II diabetes, non-alcoholic fatty liver, non-alcoholic steatohepatitis, liver steatosis, bullous steatosis, advanced fibrosis or cirrhosis; the tumor disorders comprise breast cancer, pancreatic cancer, renal cell carcinoma, hepatocellular carcinoma, malignancy melanoma and other skin tumors, non-small cell bronchial cancer, endometrial cancer, colorectal cancer, and prostate cancer.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *Chemical Drug Handbook*, 75, th Ed. 1994. Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, all of which are incorporated herein by reference in their entireties.

The term "comprise", "include" or "contain" is an open expression, it means comprising the contents disclosed herein, but don't exclude other contents.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "optionally substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "alkyl" or "alkyl group" refers to a saturated linear or branched-chain monovalent hydrocarbon radical of 1 to 20 carbon atoms, or 1-10 carbon atoms, or 1-6 carbon atoms, or 1-4 carbon atoms, or 1-3 carbon atoms, or 1-2 carbon atoms, wherein the alkyl may be optionally and independently substituted with one or more substituents described herein. Some non-limiting examples of the alkyl group further include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), n-heptyl and n-octyl, etc. The term "alkyl" or the prefix "alk-" is inclusive of both straight chain and branched saturated carbon chain. The term "alkylidene" or "alkylene" useded herein refers to a saturated divalent hydrocarbon group derived from a straight or branched chain saturated hydrocarbon by the removal of two hydrogen atoms. Examples of alkylene groups include, but are not limited to, methylene, ethylene, isopropylene, and the like.

The term "heteroatom" refers to one or more of oxygen (O), sulfur(S), nitrogen (N), phosphorus (P) and silicon (Si); including any oxidized form of carbon (C), nitrogen (N), sulfur (S), or phosphorus (P); the primary to tertiary amines and quaternary ammonium salts form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl); or —C(═O)— of heterocycle oxidated from —$CH_2$—.

The term "halogen" refers to F (fluorine), Cl (chlorine), Br (bromine), or I (iodine).

The term "unsaturated" refers to a moiety having one or more units of unsaturation.

The term "alkoxy" refers to an alkyl group, as defined herein, attached to the other moiety of the compound molecular through an oxygen atom. In some embodiments, the alkoxy group is $C_{1-4}$ alkoxy. Some non-limiting examples of the alkoxy group include methoxy, ethoxy, propoxy and butoxy, and the like. The alkoxy group may be optionally and independently substituted with one or more substituents disclosed herein.

The terms "haloalkyl", "haloalkenyl" or "haloalkoxy" refer to alkyl, alkenyl or alkoxy, as the case may be, substituted with one or more halogen atoms. In some embodiments, haloalkyl is halo $C_{1-6}$ alkyl. In other embodiments, haloalkyl is halo $C_{1-3}$ alkyl. In some embodiments, haloalkyl-oxy or haloalkoxy is halo $C_{1-6}$ alkyl-oxy or halo $C_{1-6}$alkoxy. In some embodiments, haloalkyl-oxy or haloalkoxy is halo $C_{1-3}$ alkyl-oxy or halo $C_{1-3}$ alkoxy. Some non-limiting examples of such groups include trifluoromethyl, difluoromethyl, 2-chloro-vinyl, 2,2-difluoroethyl, difluoromethoxy and trifluoromethoxy, and the like. Each of the haloalkyl, haloalkenyl or haloalkoxy may be optionally and independently substituted with one or more substituents described herein.

The term "hydroxyalkyl" or "hydroxy-substituted alkyl" refers to an alkyl group may be substituted with one or more hydroxy groups. In some embodiments, the hydroxyalkyl is hydroxy $C_{1-6}$ alkyl. In other embodiments, the hydroxyalkyl is hydroxy $C_{1-3}$ alkyl. Some non-limiting examples include hydroxymethyl, 2-hydroxyethyl, 3-hydroxypropyl, and the like. The hydroxyalkyl group may be optionally and independently substituted with one or more substituents disclosed herein.

The term "cyanoalkyl" refers to an alkyl group may be substituted with one or more cyano groups. In some embodiments, the cyanoalkyl is cyano $C_{1-6}$ alkyl. In other embodiments, the cyanoalkyl is cyano $C_{1-3}$ alkyl. Some non-limiting examples of such group included cyanomethyl, 2-cyanoethyl and 3-cyanopropyl, etc. The "cyanoalkyl" group may be independently and optionally substituted by one or more substituents disclosed herein.

The term "alkylamino" refers to "N-alkylamino" and "N,N-dialkylamino", wherein amino groups are independently substituted with one alkyl radical or two alkyl radicals, respectively. In some embodiments, the alkylamino is $C_{1-6}$ alkylamino group or ($C_{1-6}$ alkyl)amino group. In other embodiments, the alkylamino is $C_{1-3}$ alkylamino group or ($C_{1-3}$ alkyl)amino group. Some non-limiting examples of such group include N-methylamino, N-ethylamino, N,N-dimethylamino, N,N-diethylamino, and the like. And wherein the alkylamino group is optionally substituted with one or more substituents described herein.

The term "cycloalkyl" or "cycloalkane" refers to a monovalent or multivalent saturated ring having 3 to 12 carbon atoms as a monocyclic, bicyclic, or tricyclic ring system, but not containing an aromatic ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. Some non-limiting examples of such group include cyclopropyl, cyclobutyl, cyclopentyl, cyclohexyl and the like. The cycloalkyl group may be optionally substituted with one or more substituents disclosed herein.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is heteroatom, but not containing an aromatic ring. In one embodiment, "heterocycle", "heterocyclyl", or "heterocyclic ring" contains 3-10 ring atoms; in one embodiment, "heterocycle", "heterocyclyl", or "heterocyclic ring" contains 3-8 ring atoms; in another embodiment, "heterocycle", "heterocyclyl", or "heterocyclic ring" contains 5-8 ring atoms; in yet another embodiment, "heterocycle", "heterocyclyl", or "heterocyclic ring" contains 3-6 ring atoms; in still another embodiment, "heterocycle", "heterocyclyl", or "heterocyclic ring" contains 5-6 ring atoms; in another embodiment, "heterocycle", "heterocyclyl", or "heterocyclic ring" contains 4-6 ring atoms. Unless specified otherwise, heterocyclyl may be carbon radical or nitrogen radical. Hetero atom has the definition described herein. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione. Some non-limiting examples of heterocyclyl wherein the sulfur atom is oxidized is sulfolanyl and 1,1-dioxo-thiomorpholinyl. The heterocyclyl group may be optionally substituted with one or more substituents disclosed herein.

The term "heterocyclylalkyl" refers to a heterocyclyl group attached to the rest of the molecule through an alkyl group, wherein the heterocyclyl and alkyl are as defined herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic". Examples of aryl ring may include phenyl, naphthyl and anthracene. The aryl group may be independently and optionally substituted by one or more substituents disclosed herein.

The term "heteroaryl" refers to monocyclic, bicyclic and tricyclic carbocyclic ring systems having a total of five to twelve ring members, or five to ten ring members, or five to six ring members, wherein at least one ring in the system is aromatic, and in which at least one ring member is selected from heteroatom, and wherein each ring in the system contains 5 to 7 ring members and that has a single point or multipoint of attachment to the rest of the molecule. The term "heteroaryl" and "heteroaromatic ring" or "heteroaromatic compound" can be used interchangeably herein. The heteroaryl group is optionally substituted with one or more substituents disclosed herein. In one embodiment, 5-10 membered heteroaryl comprises 1, 2, 3 or 4 heteroatoms independently selected from O, S and N, wherein N may be oxidated.

Some non-limiting examples of the heteroaryl group include furanyl, imidazolyl (such as N-imidazolyl, 2-imidazolyl, 4-imidazolyl, 5-imidazolyl), isoxazolyl, oxazolyl (such as 2-oxazolyl, 4-oxazolyl, 5-oxazolyl), pyrrolyl (such as N-pyrrolyl, 2-pyrrolyl, 3-pyrrolyl), pyridyl, pyrimidinyl, pyridazinyl, thiazolyl (such as 2-thiazolyl, 4-thiazolyl, 5-thiazolyl), tetrazolyl, triazolyl, thienyl (such as 2-thienyl, 3-thienyl), pyrazolyl, isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, pyrazinyl, 1,3,5-triazinyl, and the following bicycles: benzimidazolyl, benzofuryl, benzothienyl, indolyl (such as 2-indolyl), purinyl, quinolinyl (such as 2-quinolinyl, 3-quinolinyl, 4-quinolinyl), 1,2,3,4-tetrahydroisoquinolinyl, 1,3-benzodioxolyl, indolinyl, isoquinolinyl (such as 1-isoquinolinyl, 3-isoquinolinyl or 4-isoquinolinyl), and the like.

The term "fused ring" or "fused ring group" refers to a monovalent or multivalent saturated or partially unsaturated fused ring system, and the fused ring system refers to a non-aromatic bicyclic ring system. The fused ring system may be a fused carbocyclic ring or a fused heterocyclic ring. Such system may contain independent or conjugated unsaturated system, but their core structure does not contain aromatic ring. Some non-limiting examples of the fused ring include octahydrocyclopentadienyl, hexahydro-1H-pyrinyl, hexahydropyrrole[2,1-b]oxazolyl, hexahydropyrrole[1,2-c]oxazolyl, octahydrocyclopenteno[c]pyrrolyl, hexahydro-1H-cyclopenteno[c]furanyl, hexahydro-1H-furan[3, 4-c]pyrrolyl, hexahydrofuran[3, 2-b] furanyl, and the like. And wherein the fused ring group is optionally substituted with one or more substituents described herein.

As described in the present invention, a ring system (as shown in formula a) formed by connecting a link to the ring means that the link can be connected to the rest of the molecule at any linkable position on the ring system. The formula a represents that any possible connection position on the octahydrocyclopenteno[c]pyrrole ring can be connected to the rest of the molecule.

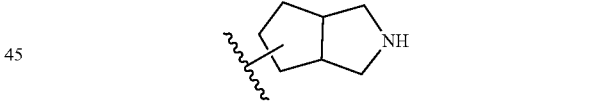

(a)

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals.

Unless otherwise stated, structures and the compound depicted herein are also meant to include all isomeric (e.g., enantiomeric, diastereomeric, and geometric (conformational isomerism)) forms of the structure, an N-oxide, a hydrate, a solvate, a metabolite, a pharmaceutically acceptable salt or a prodrug thereof. Therefore, single stereochemical isomers, enantiomeric isomerrs, diastereomeric isomerrs, geometric isomerrs, conformational isomerrs, N-oxide, a hydrate, a solvate, a metabolite, a pharmaceutically acceptable salt or a prodrug thereof of the present compounds are within the scope disclosed herein. Additionally, unless otherwise stated, structures depicted herein are also meant to include compounds that differ only in the presence of one or more isotopically enriched atoms.

"Metabolite" depicted herein which show the similar active with compound of Formula (I) in vivo or in vitro is a product produced through metabolism in the body of a specified compound or pharmaceutically acceptable salt, analogue or ramification thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker Ed., McGraw-Hill Dictionary of Chemical Terms (1984) McGraw-Hill Book Company, New York and Eliel et al., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994.

A part of the asymmetric atom (e.g., carbon or the like) of the compound(s) disclosed herein can be present in racemic or enantiomerically enriched, such as (R)-, (S)- or (R, S)-configuration; a part of the asymmetric atom can be present in a single configuration, such as (R)- or (S)-configuration. In some embodiments, the compounds provided herein comprise one, two, three, or four chiral carbons of a single configuration. In some embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and synthesis procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. Any resulting mixtures of stereoisomers can be separated on the basis of the physicochemical differences of the constituents, into the pure or substantially pure geometric isomers, enantiomers, diastereomers.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aubé, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, IN 1972); Chiral Separation Techniques: A Practical Approach (Subramanian, G Ed., Wiley-VCH Verlag GmbH & Co. KGaA, Weinheim, Germany, 2007).

The term "pharmaceutically acceptable salts" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, propionate, p-toluenesulfonate, undecanoate, valerate, and the like. Salts derived from appropriate bases include alkali metal, alkaline earth metal, ammonium and $N^+(C_{1-4} alkyl)_4$ salts. This invention also envisions the quaternization of any basic nitrogen-containing groups of the compounds disclosed herein. Water or oil soluble or dispersable products may be obtained by such quaternization. Alkali metal or alkaline earth metal that can form salts include sodium, lithium, potassium, calcium, magnesium, and the like. Further pharmaceutically acceptable salts include appropriate and nontoxic ammonium, quaternary ammonium, and amine cations formed using counterions, such as halide, hydroxide, carboxylate, sulfate, phosphate, nitrate, $C_{1-8}$ sulfonate or aryl sulfonate.

The term "hydrate" refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I) containing hydroxy group, The term "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, Advanced Organic Chemistiy, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery,* 2008, 7, 255-270, and S. J. Hecker et al, Prodrugs of Phosphates and Phosphonates, *Journal of Medicinal Chemistry,* 2008, 51, 2328-2345.

The term "therapeutically effective amount" refers to an amount of the compound of Formula (I) which is sufficient to achieve the stated effect. Accordingly, a therapeutical effective amount of a compound of formula (I) used in for the treatment of diseases regulated by ACC will be an amount sufficient for the treatment of the diseases regulated by ACC.

The terms "a", "an", "the" and similar terms used in the context of the present invention (especially in the context of the claims) are to be construed to cover both the singular and plural unless otherwise indicated herein or clearly contradicted by the context.

DESCRIPTION OF COMPOUNDS OF THE INVENTION

The present invention provides a compound or a pharmaceutical composition thereof, which can be used as an inhibitor of ACC. The present invention further provides use of the compound or the pharmaceutical composition thereof in the manufacture of a medicament for treating diseases and/or disorders by inhibiting ACC activity with the compound. The present invention further describes the synthetic method of the compound. The compound of the invention shows improved bioactivity and pharmacokinetic properties.

The present invention provides a compound having Formula (I) or an N-oxide, a hydrate, a solvate, a metabolite, a pharmaceutically acceptable salt or a prodrug thereof,

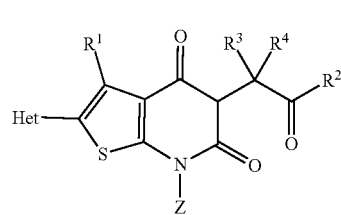

(I)

wherein, Z, Het, $R^1$, $R^2$, $R^3$ and $R^4$ are as defined herein.

In some embodiments. Z has the following structures:

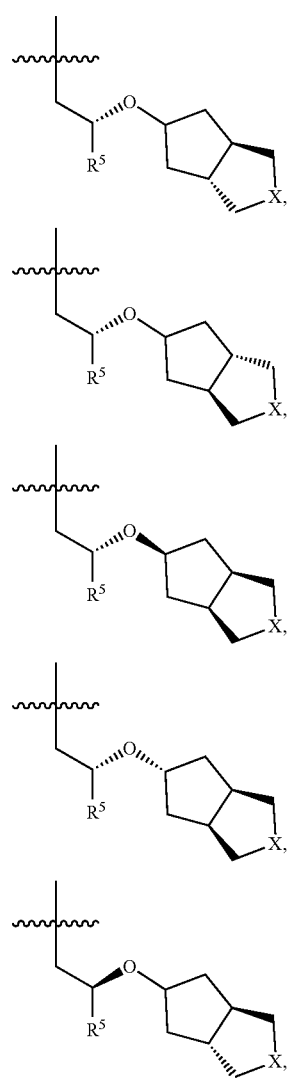

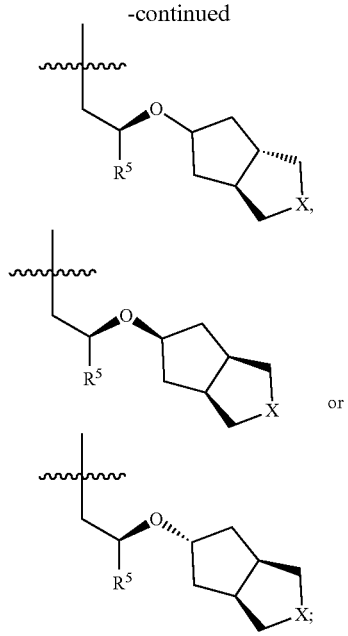

wherein $R^5$ and X are as defined herein.

In some embodiments, Het is 3-10 membered heterocyclyl or 5-10 membered heteroaryl, the 3-10 membered heterocyclyl and 5-10 membered heteroaryl can be optionally substituted by 1, 2, 3 or 4 substituents independently selected from H, D, oxo (=O), F, Cl, Br, I, hydroxyl, amino, nitro, cyano, $C_{1-6}$ alkyl, $C_{1-6}$ alkoxy, $C_{1-6}$ haloalkyl and carboxyl.

In some embodiments, the Het is pyrrolidinyl, tetrahydrofuranyl, tetrahydroimidazolyl, tetrahydropyrazolyl, tetrahydropyranyl, piperidinyl, piperazinyl, morpholinyl, thiomorpholinyl, pyrrolyl, furyl, thienyl, pyrazolyl, imidazolyl, oxazolyl, thiazolyl, triazolyl, tetrazolyl, pyridyl, pyrimidinyl, pyridazinyl or pyrazinyl; wherein, the Het can be optionally substituted by 1, 2, 3 or 4 substituents independently selected from H, D, oxo (=O), F, Cl, Br, I, hydroxyl, amino, nitro, cyano, methyl, ethyl, isopropyl, methoxy, ethoxy, isopropyloxy, trifluoromethyl, difluoromethyl and carboxyl.

In some embodiments, the Het is

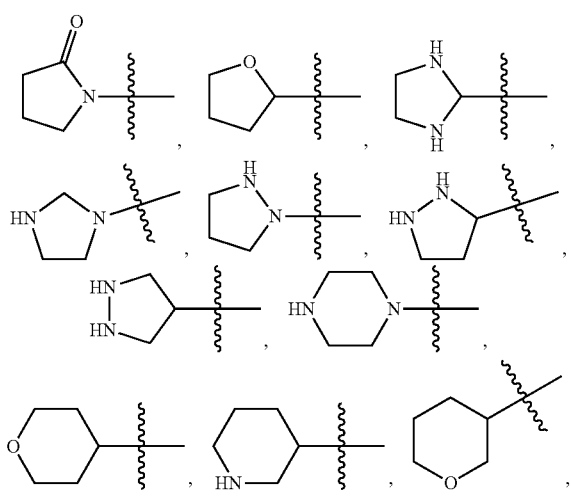

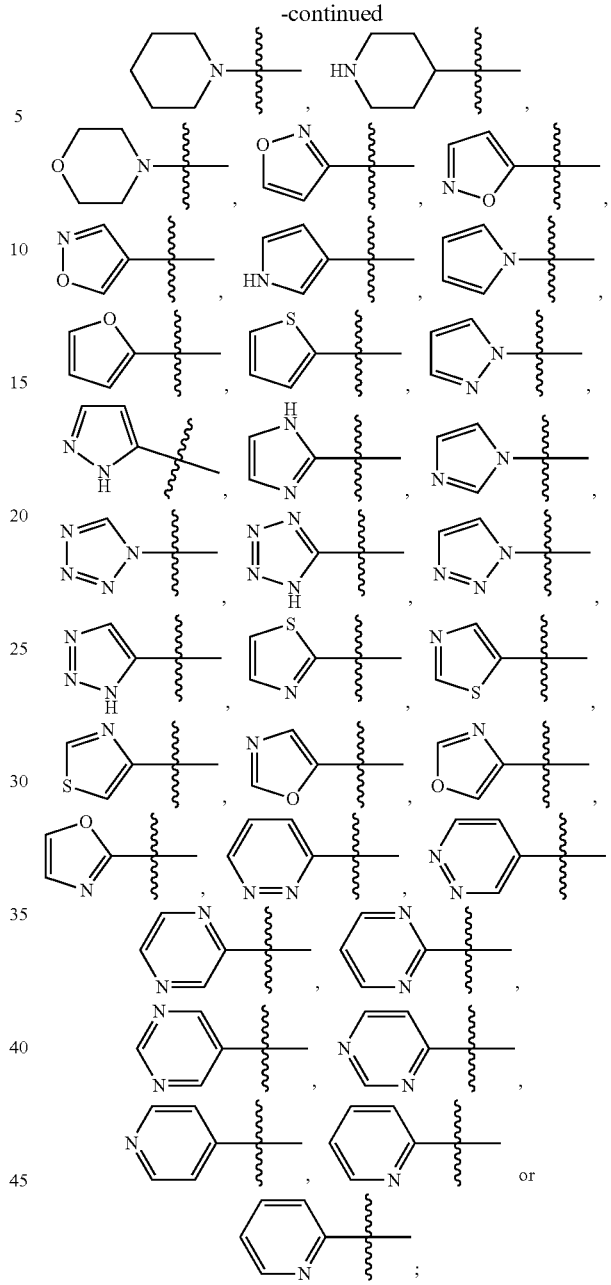

wherein, the Het can be optionally substituted by 1, 2, 3 or 4 substituents independently selected from H, D, oxo (=O), F, Cl, Br, I, hydroxyl, amino, nitro, cyano, methyl, ethyl, isopropyl, methoxy, ethoxy, isopropyloxy, trifluoromethyl, difluoromethyl and carboxyl.

In some embodiments, $R^1$ is H, D, F, Cl, Br, I, hydroxyl, amino, nitro, cyano, $C_{1-6}$ alkyl, $C_{1-6}$ alkoxy or $C_{1-6}$ haloalkyl.

In some embodiments, $R^1$ is H, D, F, Cl, Br, I, hydroxyl, amino, nitro, cyano, methyl, ethyl, methoxy, ethoxy, isopropyloxy or trifluoromethyl.

In some embodiments, $R^2$ is —OR or —NR$^a$R$^b$; and R, R$^a$ and R$^b$ are as defined herein.

In some embodiments, R, R$^a$ and R$^b$ is H, D, $C_{1-6}$ alkyl, $C_{1-6}$ alkoxy, $C_{3-6}$ cycloalkyl or $C_{1-6}$ haloalkyl.

In some embodiments, each R, R$^a$ and R$^b$ is independently H, D, methyl, ethyl, methoxy, ethoxy, cyclopropyl, cyclobutyl, cyclopentyl or cyclohexyl.

In some embodiments, $R^a$ and $R^b$, together with the N atom to which they are attached, form 4-6 membered heterocyclyl, and the 4-6 membered heterocyclyl can be optionally substituted by 1, 2, 3 or 4 substituents independently selected from oxo (=O), D, F, Cl, Br, I, hydroxy, amino, nitro, cyano, $C_{1-3}$ alkyl $C_{1-3}$ alkoxy and $C_{1-3}$ haloalkyl.

In some embodiments, $R^a$ and $R^b$, together with the N atom to which they are attached, form 4-6 membered heterocyclyl, and the 4-6 membered heterocyclyl is selected from:

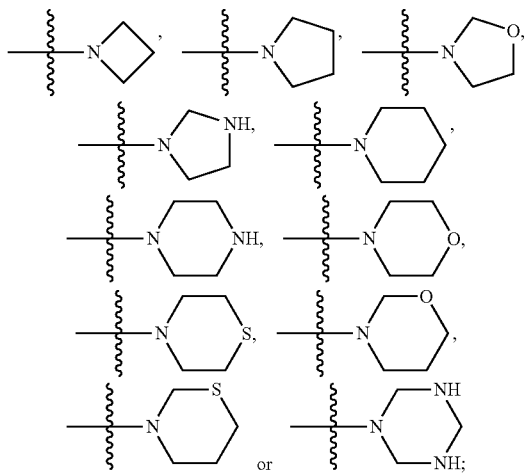

the 4-6 membered heterocyclyl can be optionally substituted by 1, 2, 3 or 4 substituents independently selected from oxo (=O), D, F, Cl, Br, I, hydroxyl, amino, nitro, cyano, methyl, ethyl, isopropyl, methoxy, ethoxy, trifluoromethyl, difluoromethyl and trifluoroethyl.

In some embodiments, each $R^3$ and $R^4$ is independently H, D, $C_{1-6}$ alkyl, $C_{1-6}$ hydroxyalkyl, or $C_{1-6}$ haloalkyl.

In some embodiments, each $R^3$ and $R^4$ is independently H, D, methyl, ethyl, n-propyl, hydroxymethyl, difluoromethyl, trifluoromethyl or 2-hydroxyethyl.

In some embodiments, $R^5$ is independently $C_{6-10}$ aryl or 5-10 membered heteroaryl, and the $C_{6-10}$ aryl and 5-10 membered heteroaryl can be optionally substituted by 1, 2 or 3 $R^6$; wherein $R^6$ is as defined herein.

In some embodiments, $R^5$ is independently phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl; wherein the phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl and pyridazinyl can be optionally substituted by 1, 2 or 3 $R^6$; wherein $R^6$ is as defined herein.

In some embodiments, each $R^6$ is independently H, D, F, Cl, Br, I, hydroxyl, amino, nitro, cyano, $C_{1-6}$ alkyl, $C_{1-6}$ alkoxy, $C_{1-6}$ haloalkyl, $C_{1-6}$ haloalkoxy, $C_{1-6}$ cyanoalkyl or $C_{1-6}$ hydroxyalkyl.

In some embodiments, each $R^6$ is independently H, D, F, Cl, Br, I, hydroxyl, amino, nitro, cyano, methyl, ethyl, n-propyl, isopropyl, methoxy, ethoxy, trifluoromethyl, difluoromethyl, trifluoromethoxy, difluoromethoxy, hydroxymethyl or 2-hydroxyethyl.

In some embodiments, X is O or $NR^7$.

In some embodiments, $R^7$ is independently H, D, F, Cl, Br, I, hydroxyl, amino, nitro, cyano, —C(=O)OH, —$SO_2R^c$, $C_{1-6}$ alkyl, $C_{3-6}$ cycloalkyl, $C_{1-6}$ alkoxy, $C_{1-6}$ haloalkoxy, $C_{1-6}$ alkylamino, $C_{1-6}$ haloalkyl, $C_{1-6}$ cyanoalkyl or $C_{1-6}$ hydroxyalkyl.

In some embodiments, $R^c$ is H, D, $C_{1-6}$ alkyl, $C_{1-6}$ alkoxy, $C_{3-6}$ cycloalkyl, or $C_{1-6}$ haloalkyl.

In some embodiments, $R^c$ is H, D, $C_{1-6}$ alkyl, $C_{1-6}$ alkoxy, $C_{3-6}$ cycloalkyl, or $C_{1-6}$ haloalkyl.

In some embodiments, the compound of the present invention is Formula (IIa), Formula (IIb), Formula (IIc), Formula (IId), Formula (IIe), Formula (IIf), Formula (IIg) or Formula (IIh), or is an N-oxide, a hydrate, a solvate, a metabolite, a pharmaceutically acceptable salt or a prodrug of the compound having Formula (IIa), Formula (IIb), Formula (IIc), Formula (IId), Formula (IIe), Formula (IIf), Formula (IIg) or Formula (IIh),

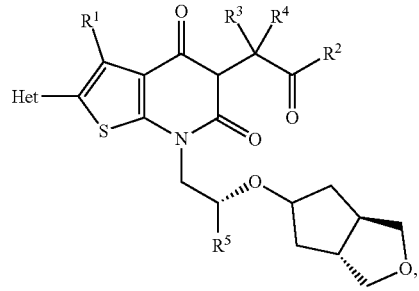

(IIa)

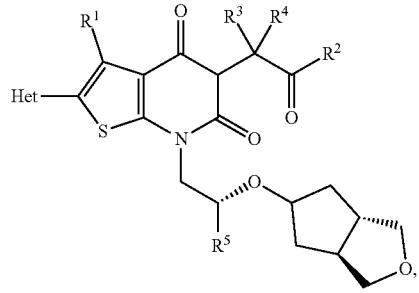

(IIb)

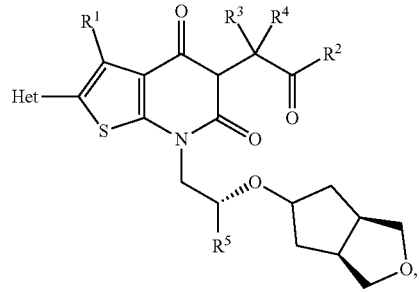

(IIc)

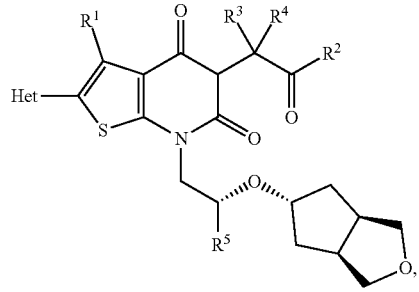

(IId)

-continued
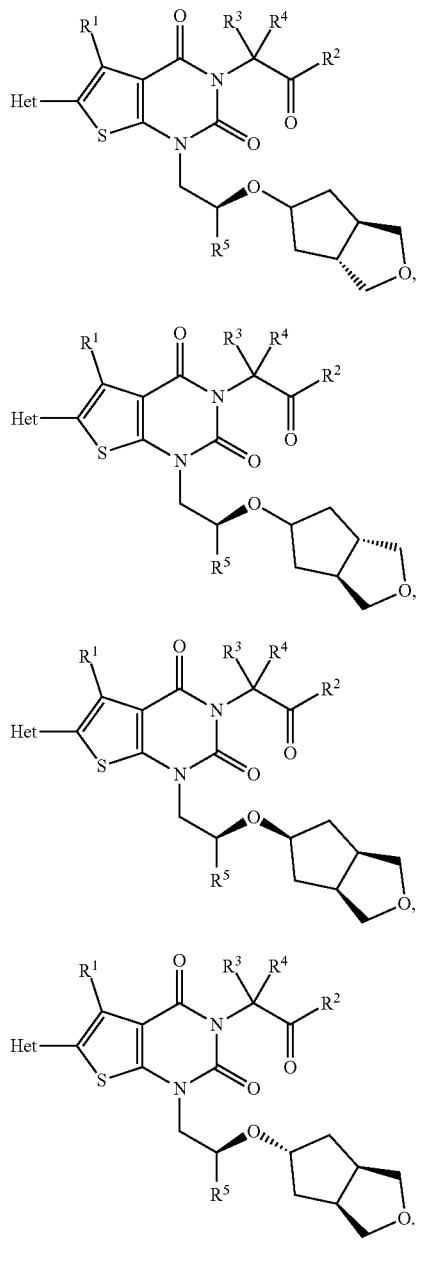
In some embodiments, the compound of the present invention is Formula (III), or an N-oxide, a hydrate, a solvate, a metabolite, a pharmaceutically acceptable salt or a prodrug thereof,
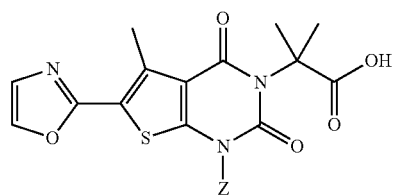
wherein, Z has the structures as described herein.
In some embodiments, the compound provided herein has one of the following structures:
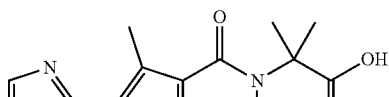
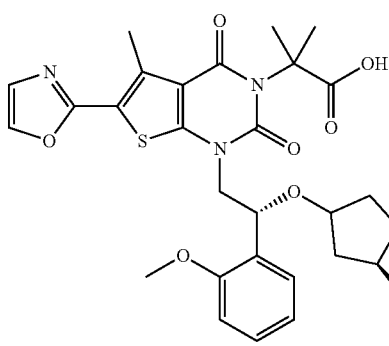
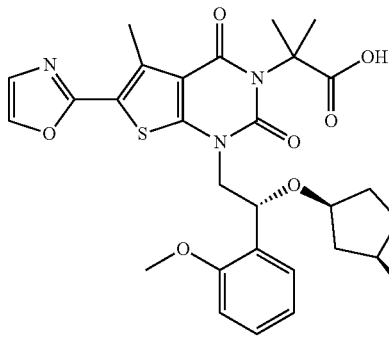
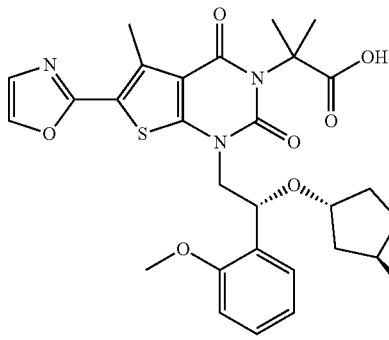

(5)
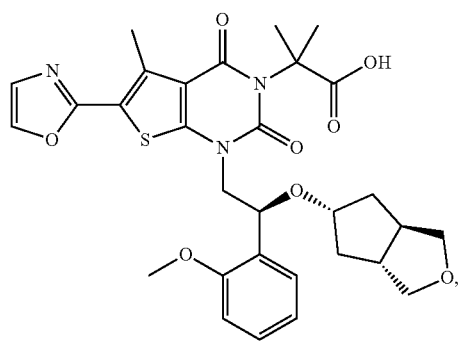
(6)
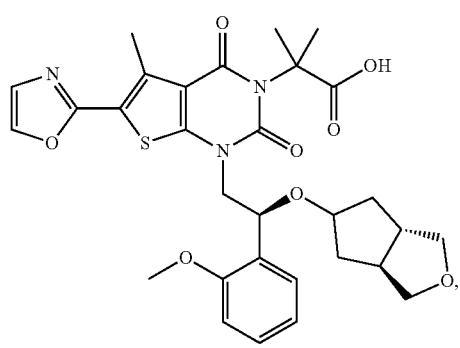
(7)
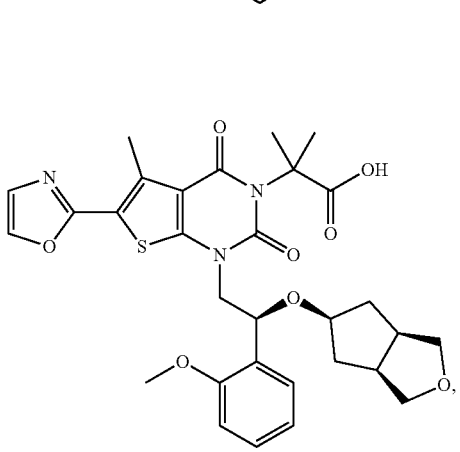
(8)
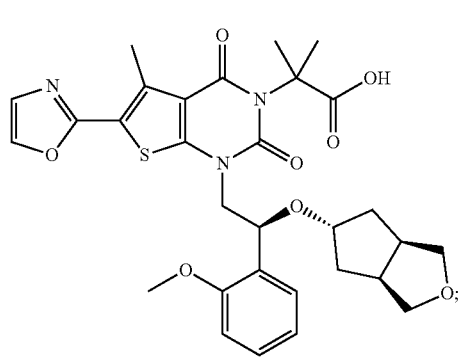
or an N-oxides, a solvate, a hydrate, a metabolite, an ester, a pharmaceutically acceptable salt or a prodrug thereof.
In other embodiments, the compound provided herein has one of the following structures:
(9)
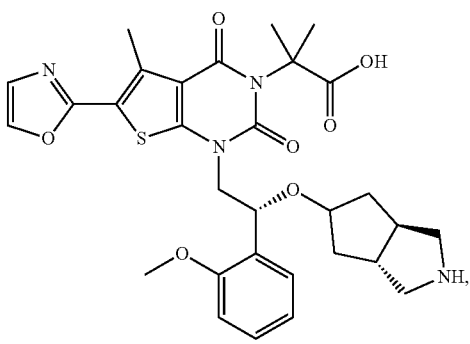
(10)
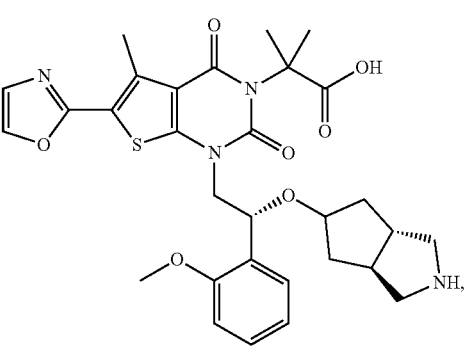
(11)
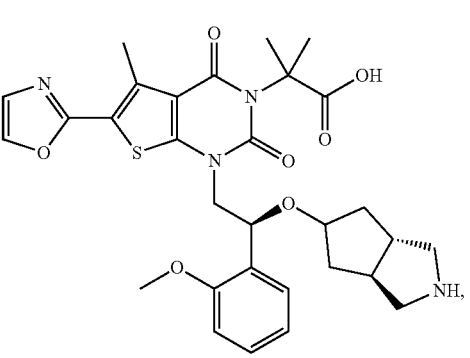
(12)
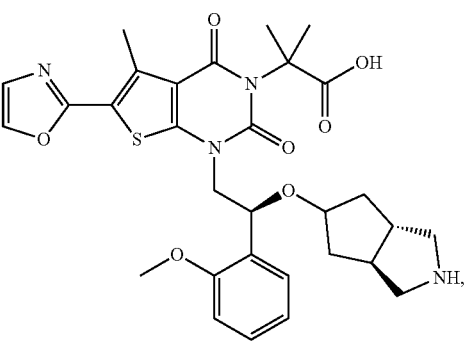

-continued
(13)
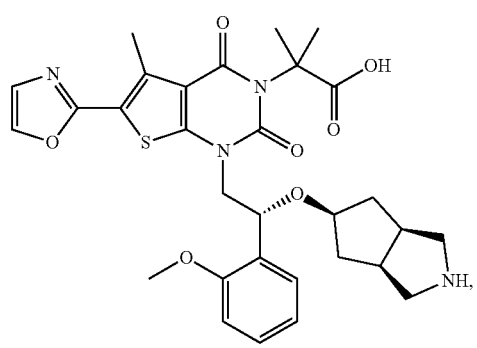
(14)
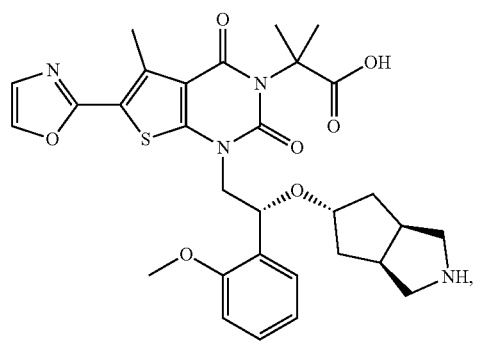
(15)
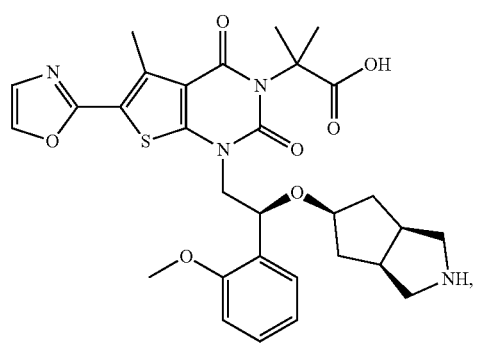
(16)
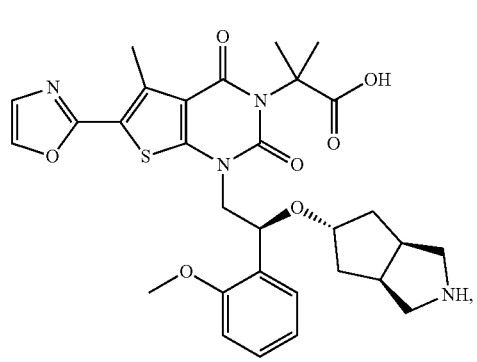
-continued
(17)
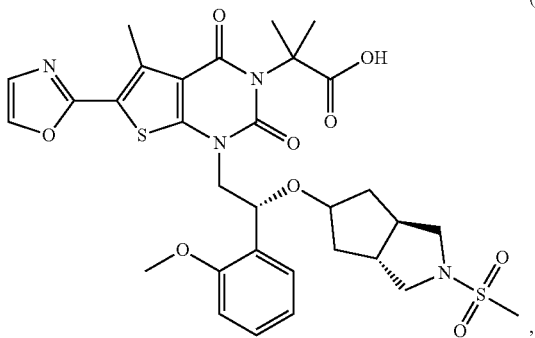
(18)
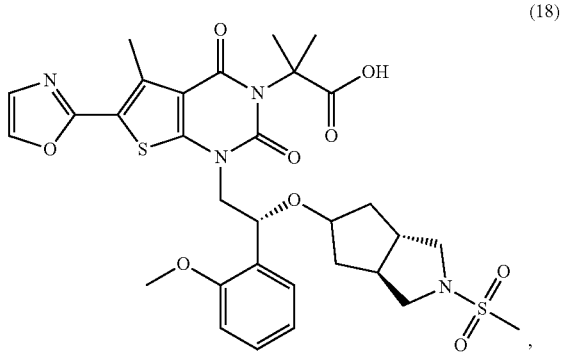
(19)
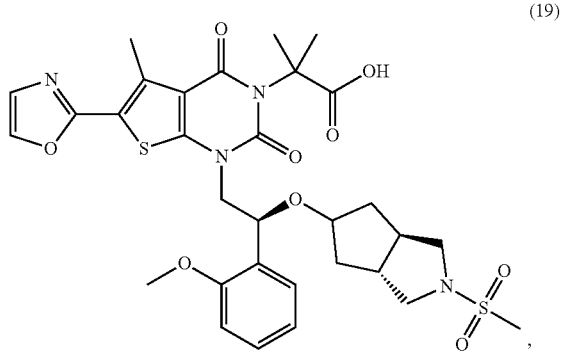
(20)
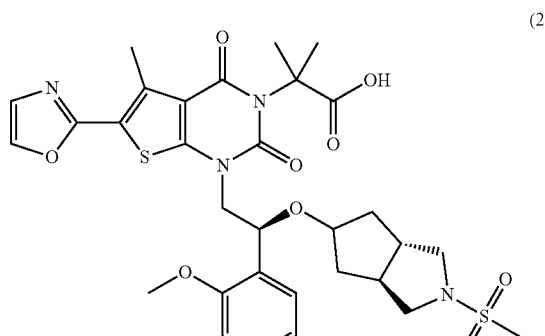

(21)

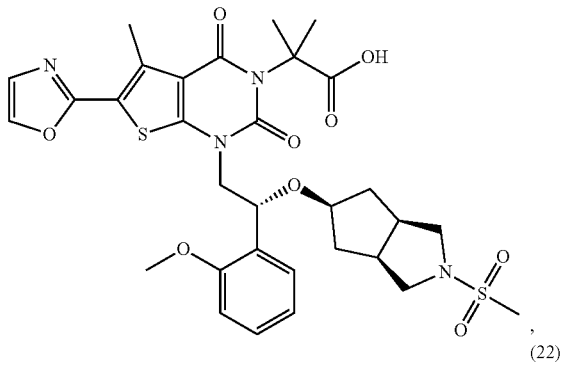

(22)

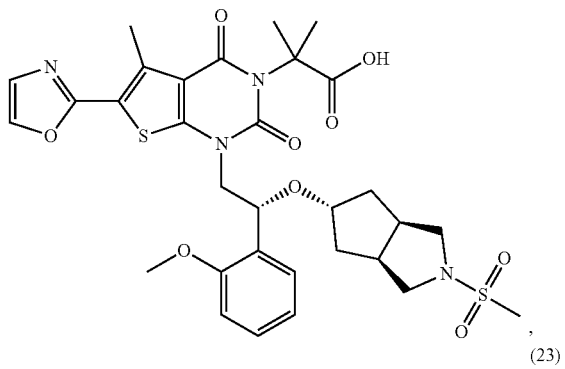

(23)

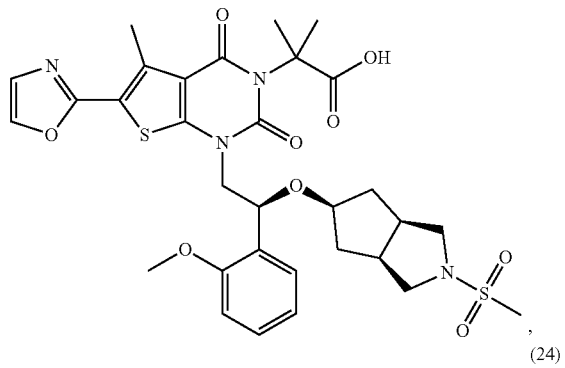

(24)

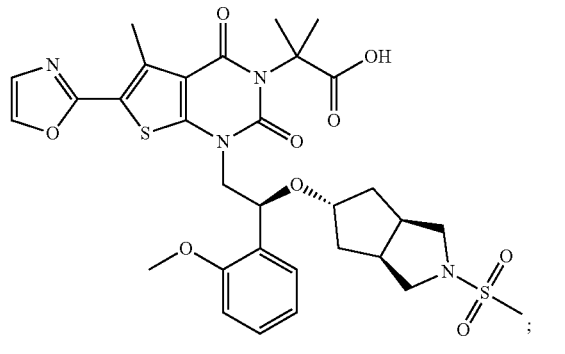

or an N-oxide, a hydrate, a solvate, a metabolite, a pharmaceutically acceptable salt or a prodrug thereof.

In some embodiments, the compounds provided herein comprise one, two, three, or four chiral carbons of a single configuration.

In one aspect, provided herein is a pharmaceutical composition comprising a stereoisomer, a geometric isomer, a tautomer, an N-oxide, a hydrate, a solvate, a metabolite, a pharmaceutically acceptable salt or a prodrug of the compound having Formula (I) disclosed herein, and a pharmaceutically acceptable carrier, an excipient, a diluent, an adjuvant, a vehicle or a combination thereof.

In one aspect, provided herein is use of the compound or the pharmaceutical composition disclosed herein in the manufacture of a medicament for preventing, treating or lessening diseases regulated by ACC.

In some embodiments, the diseases regulated by ACC of the present invention are metabolic disorders and tumor disorders.

In other embodiments, the metabolic disorders comprise insulin resistance, obesity, dyslipidemia, metabolic syndrome, type II diabetes, non-alcoholic fatty liver, non-alcoholic steatohepatitis, liver steatosis, bullous steatosis, advanced fibrosis or cirrhosis.

In other embodiments, the tumor disorders comprise breast cancer, pancreatic cancer, renal cell carcinoma, hepatocellular carcinoma, malignancy melanoma and other skin tumors, non-small cell bronchial cancer, endometrial cancer, colorectal cancer, and prostate cancer.

In one aspect, provided herein is a method of preventing, managing, treating or lessening diseases regulated by ACC, comprising administering to a patient a pharmaceutically acceptable effective dose of the compound disclosed herein.

In other aspect, provided herein is a method of preparing, separating or purifying the compound contained in the compound of Formula (I).

Pharmaceutical Composition, Formulation, Administration of the Compound of the Invention and Use of the Compound and Pharmaceutical Composition The pharmaceutical composition of the present invention is characterized by comprising the compound having Formula (I), the compounds disclosed in the present invention, and a pharmaceutically acceptable carrier, an adjuvant, or an excipient. The amount of the compound in the pharmaceutical composition of the present invention can be effectively and detectably for treating or lessening the disease regulated by ACC in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutical compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the following: In Remington: Troy et al., Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

The compound of the present invention can be used as an active ingredient and uniformly combined in a mixture with a drug carrier according to conventional drug compounding technology. The carrier can be in various forms according to the formulation required for administration, such as oral or parenteral (including intravenous). When preparing a composition for oral dosage form, any conventional pharmaceutical medium can be used, for example, water, glycol, oil, alcohol, fragrance, preservative, colorant, etc., can be used when preparing oral liquid medicaments such as suspensions, elixirs and solutions; or, for example, starch, sugar, microcrystalline cellulose, diluents, granulating agents, lubricants, binders, disintegrants, etc., can be used in the preparation of oral solid preparations such as powders, hard capsules, soft capsules and tablets, among which solid oral preparations are more preferable than liquid pharmaceuticals.

Because tablets and capsules are easy to take, they represent the most advantageous oral dosage unit form, in this case solid pharmaceutical carriers are obviously used. If necessary, tablets can be coated with standard aqueous or non-aqueous techniques. Such compositions and preparations should contain at least 0.1% of active compounds. Of course, the percentage of active compounds in these compositions can be varied, and the percentage can conveniently vary from about 2% to about 60% of the unit weight. The amount of active compounds in such therapeutically useful compositions is such that an effective dosage will be obtained. The active compounds can also be administered intranasally as, for example, liquid drops or spray.

The tablets, pills, capsules, etc. may also contain: binders (such as tragacanth, gum arabic, corn starch or gelatin); excipients (such as dicalcium phosphate); disintegrants (such as corn starch, potato starch, alginic acid); lubricants (such as magnesium stearate); and sweeteners (such as sucrose, lactose or saccharin). When the dosage unit form is a capsule, it may contain a liquid carrier (such as fatty oil) in addition to the aforementioned types of materials.

A variety of other materials can be present as coatings or to modify the shape of the dosage unit. For example, tablets can be coated with shellac, sugar, or both. In addition to the active ingredients, syrups or elixirs may contain sucrose as a sweetener, methyl or propyl 4-hydroxybenzoate as preservatives, dyes and flavoring agents (for example, cherry flavored or orange flavored).

Ophthalmic formulations, eye ointments, powders, solutions and the like, are also contemplated as being within the scope of this invention.

The compound of the present invention can also be administered parenterally. A solution or suspension of these active substances can be prepared by mixing appropriately with a surfactant (such as hydroxypropyl cellulose) in water. In glycerin, liquid polyethylene glycol and mixtures thereof, and in oil, dispersants can also be prepared. Under normal conditions of storage and use, these preparations contain a preservative to prevent the growth of microorganisms.

Pharmaceutical forms suitable for injection include sterile aqueous solutions or dispersions and sterile powders for the immediate preparation of sterile injectable solutions or dispersions. In all cases, the pharmaceutical form must be sterile and must be a fluid in an easily injectable form. It must be stable under the conditions of manufacture and storage and must be preserved under conditions that resist the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable method of administration can be used to provide an effective dose of the compound of the present invention to mammals, especially humans. For example, oral, rectal, topical, parenteral, intraocular, pulmonary, and nasal administration methods can be used. Dosage forms include tablets, lozenges, dispersions, suspensions, solutions, capsules, emulsions, ointments, aerosols, and the like. Preferably compounds of the present invention are administered orally.

The therapeutically effective dosage of the compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

When using the compound of the present invention to treat or prevent the disease regulated by ACC described in the present invention, the compound of the present invention is administered at a daily dose of about 0.1 mg to about 100 mg per kilogram of animal body weight, preferably a single daily dose, or in divided doses of 2 to 6 times a day, or by continuous release, has obtained a generally satisfactory result. For most large mammals, the total daily dose is about 1.0 mg to about 1000 mg, preferably about 1 mg to about 50 mg. For a 70 kg adult, the total daily dose is generally 7 mg to about 350 mg. This dosage method can be adjusted to provide the best therapeutic effect.

The compounds, compositions, or pharmaceutically acceptable salts or hydrates thereof provided herein can be effectively used for preventing, managing, treating or lessening diseases regulated by ACC in patients, and especially treating effectively insulin resistance, obesity, dyslipidemia, metabolic syndrome, type II diabetes, non-alcoholic fatty liver, non-alcoholic steatohepatitis, etc.

General Synthetic Procedures

Generally, the compounds disclosed herein may be prepared by methods described herein, wherein the substituents are as defined for Formula (I) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Unless otherwise indicated, reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Glassware was oven dried and/or heat dried.

Column chromatography was conducted using a silica gel column. Silica gel (300-400 mesh) was purchased from Qingdao Ocean Chemical Factory. 1H NMR spectra were recorded with a Bruker 400 MHz or 600 MHz spectrometer using $CDCl_3$, $d_3$-DMSO, $CD_3OD$ or acetone-$d_6$ as solutions (reported in ppm), and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), q (quartet), dt (doublet of triplets), tt (triplet of triplets), dddd (doublet of doublet of doublet of doublets), qd (quartet of doublets), ddd (doublet of doublet of doublets), td (triplet of doublets), dq (doublet of quartets), ddt (doublet of doublet of triplets), tdd (triplet of doublet of doublets), dtd (doublet of triplet of doublets). Coupling constants, when given, were reported in Hertz (Hz).

Low-resolution mass spectral (MS) data were determined by an Agilent 6320 Series LC-MS spectrometer equipped with a G1312A binary pump and a G1316A TCC (column was operated at 30° C.). G1329A autosampler and G1315B DAD detector were applied in the analysis, and an ESI source was used in the LC-MS spectrometer.

Low-resolution mass spectral (MS) data were determined by an Agilent 6120 Series LC-MS spectrometer equipped with a G1311A quaternary pump and a G1316A TCC (column was operated at 30° C.). G1329A autosampler and G1315D DAD detector were applied in the analysis, and an ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1:

TABLE 1

| The gradient condition of the mobile phase in Low-resolution mass spectrum analysis | | |
|---|---|---|
| Time (min) | A ($CH_3CN$, 0.1% HCOOH) | B ($H_2O$, 0.1% HCOOH) |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:

| | | | |
|---|---|---|---|
| $CDCl_3$ | chloroform-d | PE | Petroleum ether |
| $CD_3OD$ | methanol-d | Pd/C, Pd—C | Palladium on activated carbon |
| DMF | N,N-dimethylformamide | TBS | Tert-butyldimethylsilyl |
| DMSO | dimethylsulfoxide | mg | milligram |
| DMSO-$d_6$ | dimethylsulfoxide-$d_6$ | M | mole per liter |
| DCM | dichloromethane | N | Equivalent concentration |
| EtOAc, EA | ethyl acetate | g | gram |
| NaOH | sodium hydroxide | mol | mole |
| MeOH | methanol | mmol | millimoles |
| $H_2O$ | water | mL | milliliter |
| HCl | Hydrogen chloride/hydrochloric acid | μL | microliter |
| OTBDPS | Tert-butyldiphenylsiloxy | THF | tetrahydrofuran |

Synthesis Scheme

The synthetic steps for preparing the disclosed compounds of the present invention are shown in the following synthetic schemes.

Wherein, the synthesis methods of intermediates P, P', P''' and intermediate M can refer to patent applications WO2018133858[00151-00156] and WO2013071169 [00583-00587].

Wherein A refers to tert-butyldiphenylsiloxy or tert-butyloxy, and X, $R^1$, $R^3$, $R^4$, $R^5$ and Het are as defined herein.

Synthesis scheme 1

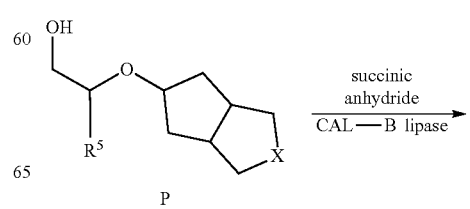

P

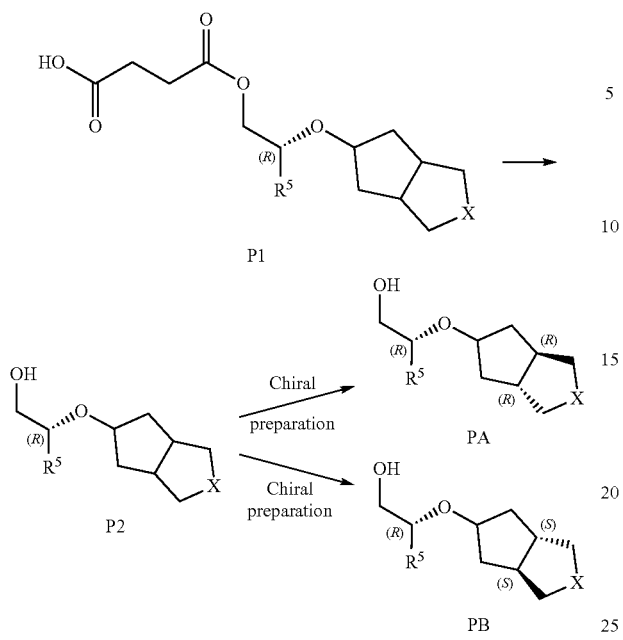

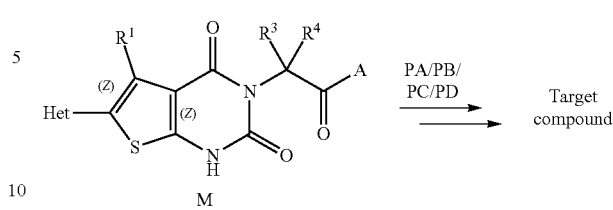

The target compound can be obtained by synthesis scheme 3: the intermediate M can be reacted with PA, PB, PC or PD, and then deesterified to obtain the target compound.

EXAMPLES

Example 1 2-[1-[(2R)-2-[[(3aR,6aR)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid Compound PA and compound PB can be obtained by synthesis scheme 1: intermediate P can be catalytically reacted with succinic anhydride and CAL-B lipase to obtain compound P1, then compound P41 can be deesterified to obtain compound P2, and finally, compound P2 can be resolved by chiral preparative column to obtain compound PA and compound PB.

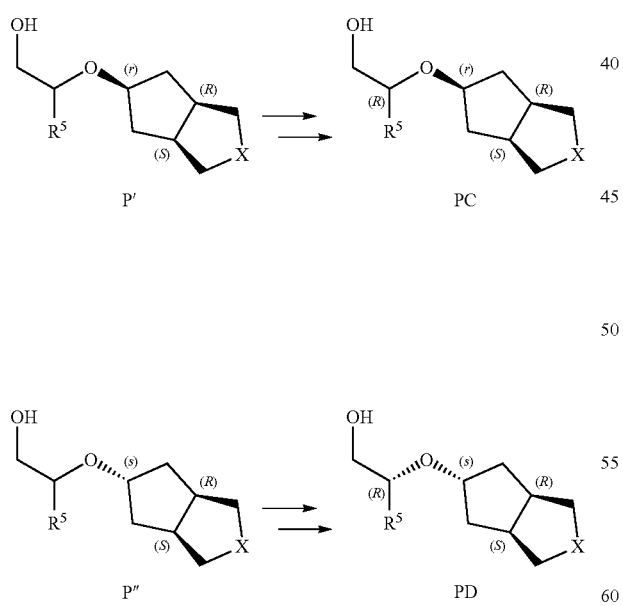

Compound PC and compound PD can be obtained by synthesis scheme 2: referring to the synthesis method of compound P2 in synthesis scheme 1, compounds P' and P'' are used as raw materials to obtain compound PC and compound PD respectively.

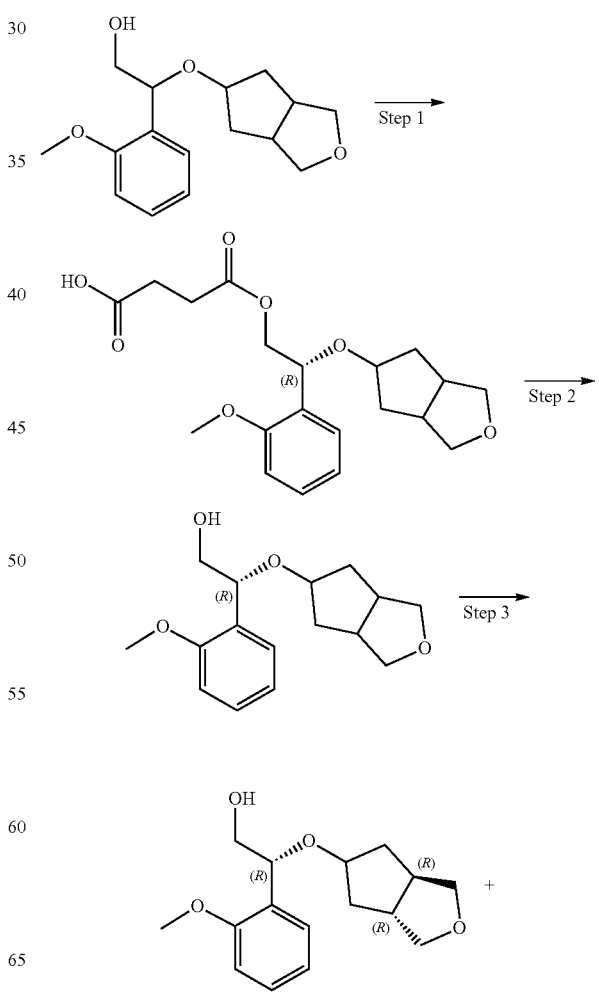

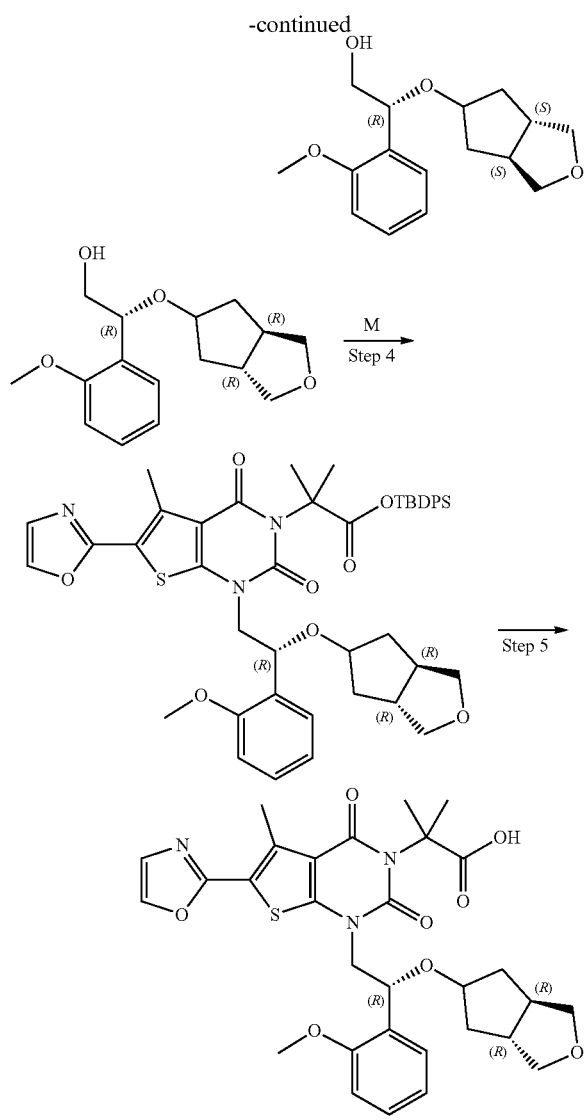

Step 1 4-[(2R)-2-(3,3a,4,5,6,6a-hexahydro-1H-cyclopenta[c]furan-5-oxy)-2-(2-methoxyphenyl)ethoxy]-4-oxo-butyric acid At room temperature, succinic anhydride (3.63 g, 35.9 mmol) was added to a solution of 2-(3,3a,4,5,6,6a-hexahydro-1H-cyclopenta[c]furan-5-oxy)-2-(2-methoxyphenyl)ethanol (10.00 g, 35.93 mmol) in tetrahydrofuran (50 mL), the mixture was stirred until the solid was completely dissolved. Then CAL-B lipase (0.70 g) was added, and the mixture was stirred and reacted overnight. The resulting mixture was filtered by suction to remove CAL-B lipase, the filtrate was concentrated and the crude product was dissolved with ethyl acetate (100 mL). The organic phase was washed with saturated sodium bicarbonate solution (80 mL×3), and the aqueous phases were combined and adjusted the pH to 3 with 3N dilute hydrochloric acid. The mixture was extracted with ethyl acetate (100 mL×2), the organic phase was washed with saturated sodium chloride solution (50 mL), and dried with anhydrous sodium sulfate, then filtered with suction and concentrated to obtain the product as a white solid (5.70 g, 41.9%).

MS (ESI, pos. ion) m/z:401.25 [M+H]$^+$;

Step 2 (2R)-2-(3,3a,4,5,6,6a-hexahydro-1H-cyclopenta[c]furan-5-oxy)-2-(2-methoxyphenyl)ethanol In an ice bath, 4-[(2R)-2-(3,3a,4,5,6,6a-hexahydro-1H-cyclopenta[c]furan-5-oxy)-2-(2-methoxyphenyl)ethoxy]-4-oxo-butyric acid (5.70 g, 15.10 mmol) was added to a sodium hydroxide aqueous solution with a mass content of 10% (70 mL), then the mixture was stirred for 2 hours. To the mixture were added water (50 mL) and ethyl acetate (100 mL) and the resulting mixture was stirred for 10 minutes, then stood and separated. The organic phase was washed with saturated sodium bicarbonate aqueous solution (50 mL) and sodium chloride aqueous solution (50 mL) in sequence, and dried with anhydrous sodium sulfate, then filtered with suction and concentrated. The residue was purified by silica gel column chromatography [petroleum ether/ethyl acetate (v/v)=1/1] to obtain the product as a white solid (2.20 g, 52.5%).

MS (ESI, pos. ion) m/z: 301.25 [M+H]+.

Step 3 (2R)-2-[[(3aR,6aR)-3,3a,4,5,6,6a-hexahydro-1H-cyclopenta[c]furan-5-yl]oxy]-2-(2-methoxyphenyl)ethanol (2R)-2-[[(3aS,6aS)-3,3a,4,5,6,6a-hexahydro-1H-cyclopenta[c]furan-5-yl]oxy]-2-(2-methoxyphenyl)ethanol (2R)-2-(3,3a,4,5,6,6a-hexahydro-1H-cyclopenta[c]furan-5-oxy)-2-(2-methoxyphen yl)ethanol (2.20 g) was resolved by chiral preparative column to obtain (2R)-2-[[(3aR,6aR)-3,3a,4,5,6,6a-hexahydro-1H-cyclopenta[c]furan-5-yl]oxy]-2-(2-methoxyphenyl)ethanol (0.700 g) and (2R)-2-[[(3aS,6aS)-3,3a,4, 5,6,6a-hexahydro-1H-cyclopenta[c]furan-5-yl]oxy]-2-(2-methoxyphenyl)ethanol (0.578 g). The preparation method was as follows: model was Daicel, IC column length was 5 um×10 mm×25 cm, column temperature was 35 degrees, mobile phase was 25% methanol: 75% carbon dioxide.

Step 4 tert-butyldiphenylsilyl 2-[1-[(2R)-2-[(3aR,6aR)-3,3a,4,5,6,6a-hexahydro-1H-cyclopenta[c]furan-5-oxy]-2-(2-methoxyphenyl)ethyl]-5-methyl-6-oxazol-2-yl-2,4-dioxo-thieno[2,3-d]pyrimidin-3-yl]-2-methyl-propanoate (2R)-2-[[(3aR,6aR)-3,3a,4,5,6,6a-hexahydro-1H-cyclopenta[c]furan-5-yl]oxy]-2-(2-methoxyphenyl)ethanol (0.375 g, 1.35 mmol), diisopropyl azodicarboxylate (0.42 mL, 2.1 mmol) and tert-butyldiphenylsilyl 2-methyl-2-(5-methyl-6-oxazol-2-yl-2,4-dioxo-1H-thieno[2,3-d]pyrimidin-3-yl)propanoate (0.850 g, 1.48 mmol) were added to tetrahydrofuran (20 mL), and triphenylphosphine (0.541 mg, 2.02 mmol) was added in batches under $N_2$. The mixture was stirred at room temperature for 19 hours. The reaction solution was concentrated under vacuum, and the residue was purified by silica gel column chromatography [petroleum ether/ethyl acetate (v/v)=2/1] to obtain the product as a white solid (0.646 g, 57.5%).

Step 5 2-[1-[(2R)-2-[[(3aR,6aR)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid Tert-butyldiphenylsilyl 2-[1-[(2R)-2-[(3aR,6aR)-3,3a,4,5,6,6a-hexahydro-1H-cyclopenta[c]furan-5-oxy]-2-(2- methoxyphenyl)ethyl]-5-methyl-6-oxazol-2-yl-2,4-dioxo-thieno[2,3-d]pyrimidine-3-yl]-2-methyl-propanoate (0.190 g, 0.228 mmol) was dissolved in tetrahydrofuran (2.0 mL), and a solution of tetrabutylammonium fluoride (1.0 mol/L) in tetrahydrofuran (0.35 mL, 0.35 mmol) was added, the mixture was stirred at room temperature for 2 hours. The reaction solution was concentrated under vacuum, and the residue was purified by silica gel column chromatography [ethyl acetate] to obtain the product as a white solid (0.071 g, 52%).

MS (ESI, pos. ion) m/z:596.3 [M+H]+;

¹H NMR (400 MHz, CDCl₃) δ 7.72 (s, 1H), 7.56-7.50 (m, 1H), 7.35-7.29 (m, 1H), 7.24 (s, 1H), 7.04 (t, J=7.4 Hz, 1H), 6.88 (d, J=8.2 Hz, 1H), 5.30-5.22 (m, 1H), 4.34-4.27 (m, 1H), 4.25-4.14 (m, 1H), 4.13-4.03 (m, 1H), 3.88 (s, 3H), 3.86-3.79 (m, 2H), 3.31-3.25 (m, 1H), 3.24-3.17 (m, 1H), 2.86 (s, 3H), 2.25-2.09 (m, 2H), 1.88 (s, 3H), 1.83 (s, 3H), 1.82-1.74 (m, 1H), 1.64-1.57 (m, 1H), 1.43-1.29 (m, 2H).

Example 2 2-[1-[(2R)-2-[[(3aS,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid

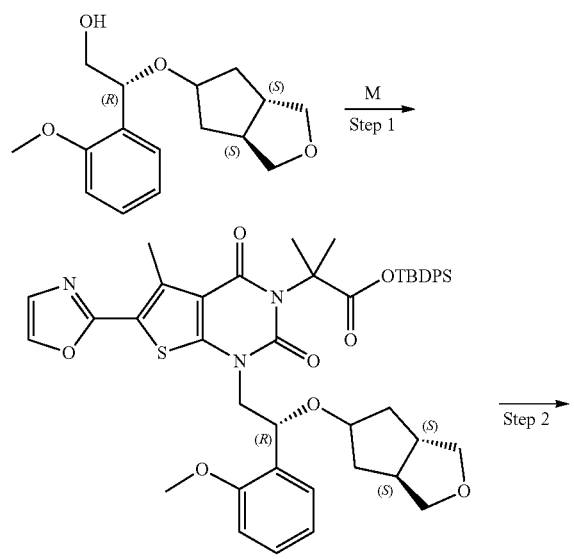

Step 1 Tert-butyldiphenylsilyl 2-[1-[(2R)-2-[(3aS,6aS)-3,3a,4,5,6,6a-hexahydro-1H-cyclopenta[c]furan-5-oxy]-2-(2-methoxyphenyl)ethyl]-5-methyl-6-oxazol-2-yl-2,4-dioxo-thieno[2,3-d]pyrimidin-3-yl]-2-methyl-propanoate (2R)-2-[[(3aS,6aS)-3,3a,4,5,6,6a-hexahydro-1H-cyclopenta[c]furan-5-yl]oxy]-2-(2-methoxyphenyl)ethanol (0.278 g, 0.999 mmol), diisopropyl azodicarboxylate (0.32 mL, 1.6 mmol) and tert-butyldiphenylsilyl 2-methyl-2-(5-methyl-6-oxazol-2-yl-2,4-dioxo-1H-thieno[2,3-d]pyrimidin-3-yl)propanoate (0.630 g, 1.10 mmol) were added to tetrahydrofuran (30 mL), and triphenylphosphine (0.401 mg, 1.50 mmol) was added in batches under N₂, the mixture was stirred at room temperature for 12 hours. The reaction solution was concentrated under vacuum, and the residue was purified by silica gel column chromatography [petroleum ether/ethyl acetate (v/v)=2/1] to obtain the product as a white solid (0.380 g, 45.6%).

Step 2 2-[1-[(2R)-24 [(3aS,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid Tert-butyldiphenylsilyl 2-[1-[(2R)-2-[(3aS,6aS)-3,3a,4,5,6,6a-hexahydro-1H-cyclopenta[c]furan-5-oxy]-2-(2-methoxyphenyl)ethyl]-5-methyl-6-oxazol-2-yl-2,4-dioxo-thieno[2,3-d]pyrimidin-3-yl]-2-methyl-propanoate (0.380 g, 0.456 mmol) was dissolved in tetrahydrofuran (6 mL), and a solution of tetrabutylammonium fluoride (1.0 mol/L) in tetrahydrofuran (0.9 mL, 0.9 mmol) was added, the mixture was stirred at room temperature for 0.5 hours. The reaction solution was concentrated under vacuum, and the residue was purified by silica gel column chromatography [ethyl acetate] to obtain the product as a white solid (0.160 g, 59%).

MS (ESI, neg. ion) m/z:594.2 [M+H]+;

¹H NMR (400 MHz, CDCl₃) δ 7.72 (s, 1H), 7.57-7.52 (m, 1H), 7.35-7.29 (m, 1H), 7.24 (s, 1H), 7.05 (t, J=7.5 Hz, 1H), 6.89 (d, 0.1=8.2 Hz, 1H), 5.28-5.22 (m, 1H), 4.42-4.35 (m, 1H), 4.23-4.15 (m, 1H), 4.11-4.04 (m, 1H), 3.89 (s, 3H), 3.84-3.78 (m, 2H), 3.29-3.24 (m, 1H), 3.23-3.17 (m, 1H), 2.87 (s, 3H), 2.33-2.21 (m, 1H), 2.17-2.10 (m, 1H), 1.89 (s, 3H), 1.84 (s, 3H), 1.83-1.73 (m, 1H), 1.49-1.40 (m, 1H), 1.36-1.32 (m, 2H).

Example 3 2-[1-[(2R)-2-[[(3aR,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid

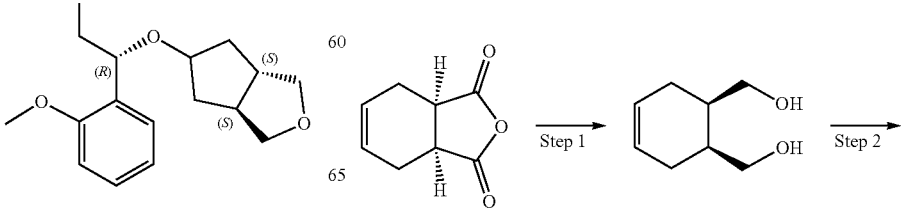

39
-continued

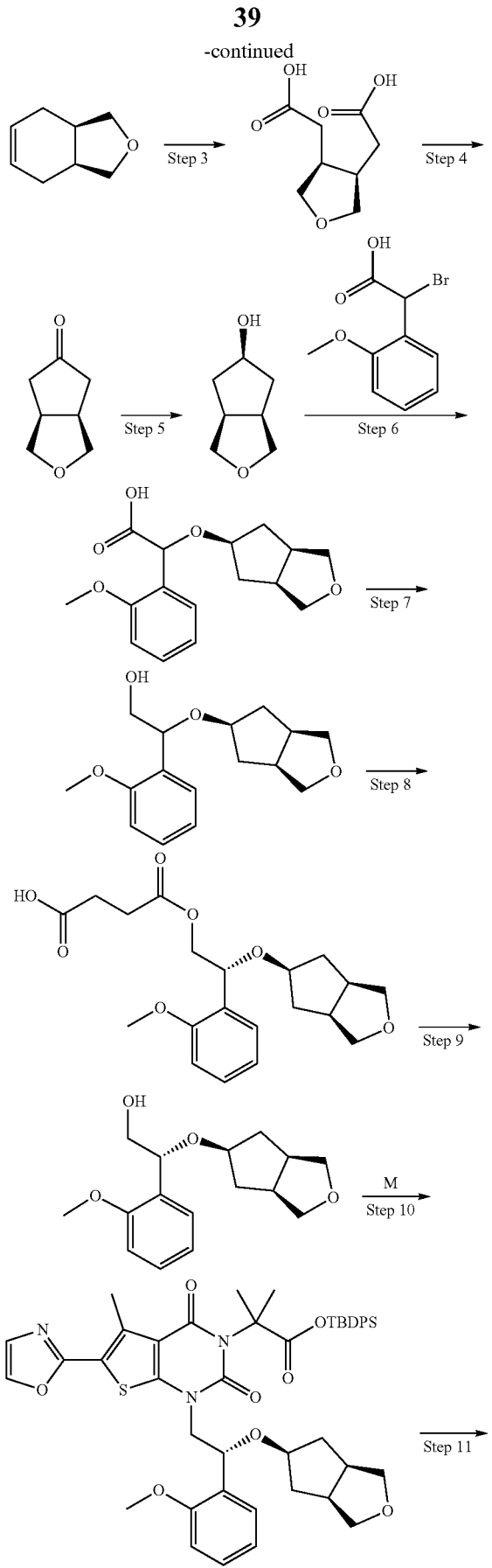

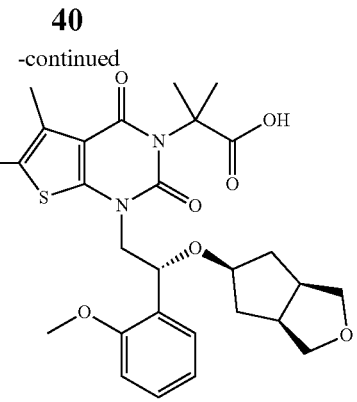

Step 1 (1R,2S)-cyclohex-4-ene-1,2-dimethanol

In an ice bath, (3aR,7aS)-3a,4,7,7a-tetrahydroisobenzofuran-1,3-dione (20.00 g, 131.45 mmol) was added to tetrahydrofuran (200 mL), and the mixture was stirred to dissolve, then lithium aluminum hydride (20.00 g, 526.945 mmol) was added in batches. After the addition, the mixture was moved to room temperature and stirred overnight. In an ice bath, to the mixture were slowly added water (20 mL), 10% sodium hydroxide aqueous solution (40 mL) and water (60 mL) dropwise in sequence, and the resulting mixture was stirred for 10 minutes, then anhydrous sodium sulfate (20.00 g) was added and stirred for 10 minutes. The mixture was filtered with suction and concentrated to obtain the product as a yellow oil (19.80 g, 100%).

Step 2 (3aR,7aS)-1,3,3a,4,7,7a-hexahydroisobenzofuran

At room temperature, (1R,2S)-cyclohex-4-ene-1,2-dimethanol (19.80 g, 139 mmol) and toluenesulfonic acid monohydrate (1.00 g, 5.69 mmol) were added in sequence to toluene (130 mL), the mixture was stirred to dissolve. Then the mixture was heated to 115° C. and removed water in a water separator, and stirred overnight. The reaction solution was concentrated under vacuum, and the residue was purified by silica gel column chromatography [petroleum ether/ethyl acetate (v/v)=8/1] to obtain the product as a yellow liquid (14.30 g, 82.7%).

$^1$H NMR (400 MHz, DMSO-d$_6$) δ 5.61 (q, J=10.3 Hz, 2H), 4.50 (t, J=4.7 Hz, 1H), 4.20-4.14 (m, 1H), 4.06-4.00 (m, 1H), 3.47-3.40 (m, 1H), 2.18-2.12 (m, 1H), 2.11-2.04 (m, 2H), 1.96-1.83 (m, 4H).

Step 3 2,2'-((3R,4S)-tetrahydrofuran-3,4-diyl)diacetic acid

At room temperature, potassium permanganate (58.80 g, 368 mmol) was added to water (345 mL), the mixture was stirred for 0.5 hours, then moved to an ice bath. A solution of (3aR,7aS)-1,3,3a,4,7,7a-hexahydroisobenzofuran (14.30 g, 115 mmol) in acetone (50 mL) was slowly added dropwise to the reaction system. After the addition, the solution was moved to room temperature and stirred overnight. In an ice bath, to the solution was slowly added saturated sodium thiosulfate (250 mL) dropwise to quench the reaction, and the resulting mixture was stirred for 0.5 hours, added with concentrated hydrochloric acid to adjust the pH at 2, then extracted with ethyl acetate/tetrahydrofuran (v/v)=1/1 (200 mL)×3). The organic phases were combined, and concentrated under vacuum to obtain the product as pale yellow liquid (19.40 g, 89.5%).

Step 4 (3aR,6aS)-1,3,3a,4,6,6a-hexahydrocyclopenta[c]furan-5-one 2,2'-((3R,4S)-tetrahydrofuran-3,4-diyl)diacetic acid (17.70 g, 94.1 mmol) and sodium acetate (7.80 g, 94 mmol) were added to acetic anhydride (100 mL), the mixture was heated to 130° C. and stirred overnight. The mixture was cooled to room temperature and concentrated under vacuum, then ethyl acetate (300 mL) was added and filtered with suction, the filtrate was concentrated under vacuum. The residue was purified by silica gel column chromatography [petroleum ether/ethyl acetate (v/v)=6/1] to obtain the product as a reddish brown oil (3.84 g, 32.4%).

Step 5 (3aR,5r,6aS)-3,3a,4,5,6,6a-hexahydro-1H-cyclopenta[c]furan-5-ol

In an ice bath, (3aR,6aS)-1,3,3a,4,6,6a-hexahydrocyclopenta[c]furan-5-one (3.84 g, 30.4 mmol) was dissolved in methanol (50 mL), then sodium borohydride (1.27 g, 33.6 mmol) was added in batches, and after the addition, the mixture was stirred at room temperature for 1 hour. To the mixture were added water (5 mL) and dilute hydrochloric acid (5 mL) in sequence to quench the reaction, the solution was concentrated under vacuum, and the residue was purified by silica gel column chromatography [petroleum ether/ethyl acetate (v/v)=4/1] to obtain the product as a reddish brown oil (1.81 g, 46.4%).

$^1$H NMR (400 MHz, CDCl$_3$) δ 4.09 (s, 1H), 3.80 (d, J=9.2 Hz, 2H), 3.61-3.55 (m, 2H), 2.81-2.69 (m, 2H), 2.02-1.95 (m, 2H), 1.67-1.62 (m, 2H).

Step 6 2-[[(3aR,5r,6aS)-3,3a,4,5,6,6a-hexahydro-1H-cyclopenta[c]furan-5-yl]oxy]-2-(2-methoxyphenyl)acetic acid In an ice bath, under N$_2$, sodium hydride (1.51 g, 56.6 mmol) was added in batches to a solution of (3aR,5r,6aS)-3,3a,4,5,6,6a-hexahydro-1H-cyclopenta[c]furan-5-ol (1.81 g, 14.1 mmol) in tetrahydrofuran (20 mL), the mixture was stirred for 0.5 hours. A solution of 2-bromo-2-(2-methoxyphenyl)acetic acid (4.15 g, 16.9 mmol) in tetrahydrofuran (30 mL) was slowly added dropwise to the system, after the addition, the mixture was moved to room temperature and stirred overnight. The resulting mixture was poured to ice water (40 mL) slowly, the aqueous phase was washed with ethyl acetate (30 mL×2) and the aqueous phases were collected, and adjusted the pH to 2 with 4N dilute hydrochloric acid aqueous solution. The mixture was extracted with ethyl acetate (40 mL×2), the organic phases were combined and washed with saturated sodium chloride aqueous solution (40 mL), and dried with anhydrous sodium sulfate, then filtered with suction and concentrated under vacuum to obtain the product as a pale yellow oil (5.53 g, 100%).

Step 7 2-[[(3aR,5r,6aS)-3,3a,4,5,6,6a-hexahydro-1H-cyclopenta[c]furan-5-yl]oxy]-2-(2-methoxyphenyl)ethanol In an ice bath, 2-[[(3aR,5r,6aS)-3,3a,4,5,6,6a-hexahydro-1H-cyclopenta[c]furan-5-yl]oxy]-2-(2-methoxyphenyl)acetic acid (5.53 g, 18.9 mmol) was dissolved in tetrahydrofuran (50 mL), and borane tetrahydrofuran solution (38 mL, 38 mmol, 1.0 mol/L) was slowly added dropwise to the reaction system, after the addition, the mixture was moved to room temperature and stirred for 4 hours. In an ice bath, methanol (30 mL) was slowly added dropwise to the reaction system to quench the reaction. After the addition, the mixture was stirred for 0.5 hours. The reaction solution was concentrated under vacuum, and the residue was purified by silica gel column chromatography [petroleum ether/ethyl acetate (v/v)=6/1] to obtain the product as a pale yellow oil (2.30 g, 44%).

MS (ESI, pos. ion) m/z: 301.2[M+Na]$^+$.

$^1$H NMR (400 MHz, CDCl$_3$) δ 7.39 (d, J=7.5 Hz, 1H), 7.23 (d, J=7.5 Hz, 1H), 6.96 (t, J=7.4 Hz, 1H), 6.85 (d, J=8.2 Hz, 1H), 4.92 (dd, J=9.1, 2.8 Hz, 1H), 3.94 (dd, J=8.8, 1.8 Hz, 1H), 3.89 (d, J=9.1 Hz, 1H), 3.85-3.82 (m, 1H), 3.81 (s, 3H), 3.72 (t, J=8.2 Hz, 1H), 3.69-3.58 (m, 2H), 3.47-3.38 (m, 1H), 2.76-2.63 (m, 2H), 2.00-1.90 (m, 1H), 1.88-1.82 (m, 3H).

Step 8 4-[(2R)-2-[[(3aR,5r,6aS)-3,3a,4,5,6,6a-hexahydro-1H-cyclopenta[c]furan-5-yl]oxy]-2-(2-methoxyphenyl)ethoxy]-4-oxo-butanoic acid 2-[[(3aR,5r,6aS)-3,3a,4,5,6,6a-hexahydro-1H-cyclopenta[c]furan-5-yl]oxy]-2-(2-methoxyphenyl)ethanol (2.30 g, 8.3 mmol) and succinic anhydride (0.83 g, 8.3 mmol) were dissolved in tetrahydrofuran (20 mL), and then CAL-B lipase (0.16 g, 7% w/w) was added, the mixture was stirred overnight at room temperature. The mixture was filtered with suction to remove CAL-B lipase, then the filtrate was concentrated under vacuum, the crude product was dissolved with ethyl acetate (100 mL), and then the organic phase was washed with saturated sodium bicarbonate aqueous solution (50 mL×3). The aqueous phases were combined, and adjusted the pH to 3 with 3N dilute hydrochloric acid, then extracted with ethyl acetate (50 mL×3). The organic phases were combined, and dried with anhydrous sodium sulfate, then filtered with suction and concentrated to obtain the product as a white solid (1.24 g, 40%).

MS (ESI, neg. ion) m/z: 377.2[M−H]$^-$.

Step 9 (2R)-2-[[(3aR,5r,6aS)-3,3a,4,5,6,6a-hexahydro-1H-cyclopenta[c]furan-5-yl]oxy]-2-(2-methoxyphenyl)ethanol 4-[(2R)-2-[[(3aR,5r,6aS)-3,3a,4,5,6,6a-hexahydro-1H-cyclopenta[c]furan-5-yl]oxy]-2-(2-methoxyphenyl)ethoxy]-4-oxo-butanoic acid (1.24 g, 3.28 mmol) was dissolved in methanol (4 mL), and then a sodium hydroxide aqueous solution with a mass content of 10% (10 mL) was added, the mixture was stirred at room temperature for 3 hours. To the mixture were added water (8 mL) and ethyl acetate (30 mL), and the resulting mixture was stirred for 10 minutes, then separated. The organic phase was washed with saturated sodium bicarbonate aqueous solution (40 mL) and saturated sodium chloride aqueous solution (40 mL) in sequence, and dried with anhydrous sodium sulfate, then filtered with suction and concentrated to obtain the product as a white solid (0.50 g, 50%).

Step 10 tert-butyldiphenylsilyl 2-[1-[(2R)-2-[[(3aR,5r,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propanoate (2R)-2-[[(3aR,5r,6aS)-3,3a,4,5,6,6a-hexahydro-1H-cyclopenta[c]furan-5-yl]oxy]-2-(2-methoxyphenyl)ethanol (200 mg, 0.719 mmol), tert-butyldiphenylsilyl 2-methyl-2-(5-methyl-6-oxazol-2-yl-2,4-dioxo-1H-thieno[2,3-d]pyrimidin-3-yl)propanoate (454 mg, 0.791 mmol) and triphenylphosphine (379 mg, 1.44 mmol) were dissolved in tetrahydrofuran (10 mL) under N₂ in an ice bath, diisopropyl azodicarboxylate (0.3 mL, 1 mmol) was slowly added to the mixture. After the addition, the mixture was moved to room temperature and stirred overnight. The reaction solution was concentrated under vacuum, and the residue was purified by silica gel column chromatography [petroleum ether/ethyl acetate (v/v)=6/1] to obtain the product as a pale yellow solid (0.59 g, 100%).

Step 11 2-[1-[(2R)-2-[[(3aR,5r,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid In an ice bath, tert-butyldiphenylsilyl 2-[1-[(2R)-2-[[(3aR,5r,6aS)-3,3a,4,5,6,6a-hexahydro-1H-cyclopenta[c]furan-5-yl]oxy]-2-(2-meth oxyphenyl)ethyl]-5-methyl-6-oxazol-2-yl-2,4-dioxo-thieno[2,3-d]pyrimidin-3-yl]-2-methyl-propanoate (0.59 g, 0.71 mmol) was dissolved in tetrahydrofuran (10 mL), then a solution of 1.0 mol/L of tetrabutylammonium fluoride in tetrahydrofuran (3 mL, 3 mmol) was slowly added dropwise to the mixture. After the addition, the mixture was moved to room temperature and stirred for 40 minutes. The reaction solution was concentrated under vacuum, and the residue was purified by silica gel column chromatography [dichloromethane/methanol (v/v)=30/1] to obtain the product as a white solid (0.13 g, 31%).

MS (ESI, neg. ion) m/z: 594.2 [M−H]⁻.

¹H NMR (400 MHz, CDCl₃) δ 7.74 (s, 1H), 7.54 (d, J=7.3 Hz, 1H), 7.32 (t, J=6.2 Hz, 1H), 7.27 (s, 1H), 7.05 (t, J=7.5 Hz, 1H), 6.90 (d, J=8.2 Hz, 1H), 5.37-5.34 (m, 1H), 4.30-4.18 (m, 1H), 4.04-3.96 (m, 1H), 3.90 (s, 3H), 3.82-3.75 (m, 1H), 3.71-3.66 (m, 2H), 3.62-3.58 (m, 1H), 3.56-3.51 (m, 1H), 2.88 (s, 3H), 2.57-2.50 (m, 2H), 1.99-1.92 (m, 2H), 1.90 (s, 3H), 1.86 (s, 3H), 1.58-1.50 (m, 1H), 1.43-1.36 (m, 1H).

Example 4 2-[1-[(2R)-2-[[(3aS,5s,6aR)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methyl-propionic acid

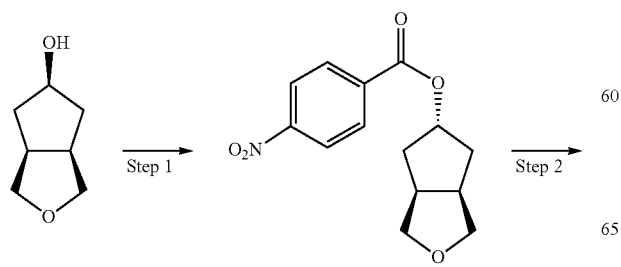

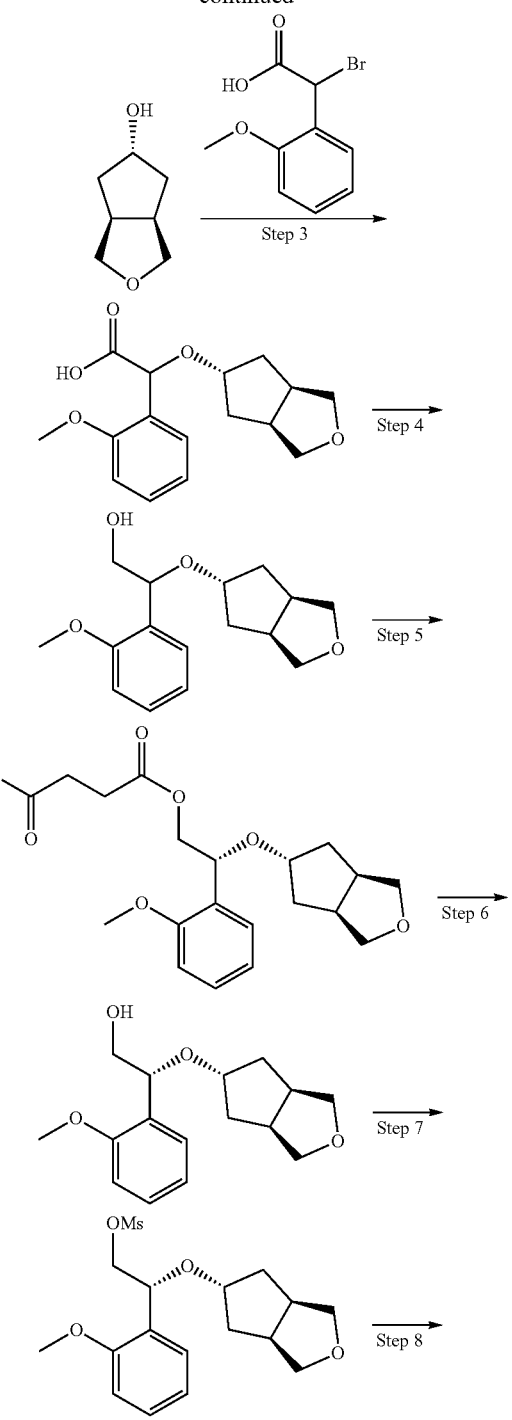

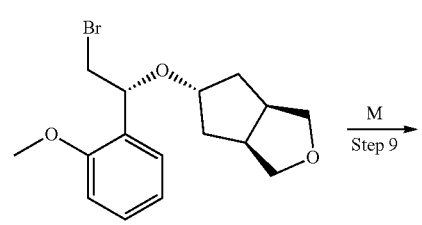

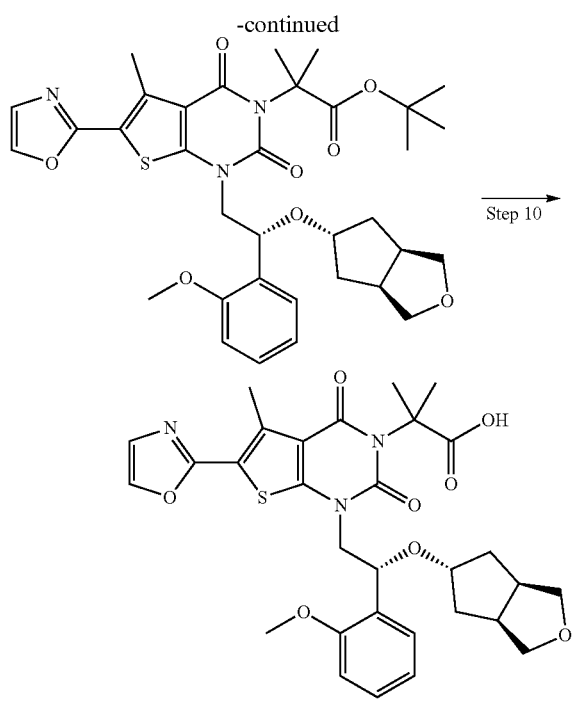

Step 1 [(3aR,5s,6aS)-3,3a,4,5,6,6a-hexahydro-1H-cyclopenta[c]furan-5-yl]4-nitrobenzoate (3aR,5r,6aS)-3,3a,4,5,6,6a-hexahydro-1H-cyclopenta[c]furan-5-ol (1.00 g, 7.8 mmol), 4-nitrobenzoic acid (3.90 g, 23.4 mmol) and triphenylphosphine (6.00 g, 23.4 mmol) were dissolved in tetrahydrofuran (50 mL). In an ice bath, diisopropyl azodicarboxylate was slowly added dropwise to the mixture. After the addition, the mixture was moved to room temperature and stirred for 2.5 hours. The reaction solution was concentrated under vacuum, and the residue was purified by silica gel column chromatography [petroleum ether/ethyl acetate (v/v)=5/1] to obtain the product as a colorless oil (2.20 g, 100%).

MS (ESI, pos. ion) m/z:379.0[M+H]$^+$.

Step 2 (3aR,5s,6aS)-3,3a,4,5,6,6a-hexahydro-1H-cyclopenta[c]furan-5-ol

At room temperature, potassium carbonate (2.20 g, 16.0 mmol) was added to a solution of [(3aR,5s,6aS)-3,3a,4,5,6,6a-hexahydro-1H-cyclopenta[c]furan-5-yl]4-nitrobenzoate (2.20 g, 7.9 mmol) in methanol (20 mL), the mixture was stirred overnight. The reaction was concentrated under vacuum, and the residue was purified by silica gel column chromatography [petroleum ether/ethyl acetate (v/v)=3/1] to obtain the product as a white solid (0.50 g, 50%).

MS (ESI, pos. ion) m/z: 129.3[M+H]$^+$.

Step 3 2-[[(3aR,5s,6aS)-3,3a,4,5,6,6a-hexahydro-1H-cyclopenta[c]furan-5-yl]oxy]-2-(2-methoxyphenyl)acetic acid In an ice bath, sodium hydride (0.60 g, 60%, 20.0 mmol) was added in batches to a solution of (3aR,5s,6aS)-3,3a,4,5,6,6a-hexahydro-1H-cyclopenta[c]furan-5-ol (0.50 g, 4.0 mmol) in tetrahydrofuran (20 mL), after the addition, the mixture was stirred for 0.5 hours. A solution of 2-bromo-2-(2-methoxyphenyl)acetic acid (1.00 g, 5.0 mmol) in tetrahydrofuran (5 mL) was slowly added dropwise to the mixture. After the addition, the mixture was moved to room temperature and stirred overnight. The resulting mixture was poured to ice water (30 mL) slowly, the aqueous phase was washed with ethyl acetate (10 mL×2) and the aqueous phases were collected, and adjusted the pH to 2 with 4N dilute hydrochloric acid aqueous solution. The mixture was extracted with ethyl acetate (20 mL×2), the organic phases were combined and washed with saturated sodium chloride aqueous solution (20 mL), and dried with anhydrous sodium sulfate, then filtered with suction and concentrated under vacuum to obtain the product as a pale yellow oil (1.60 g, 100%), which was used in the next step without further purification.

Step 4 2-[[(3aR,5s,6aS)-3,3a,4,5,6,6a-hexahydro-1H-cyclopenta[c]furan-5-yl]oxy]-2-(2-methoxyphenyl)ethanol 2-[[(3aR,5s,6aS)-3,3a,4,5,6,6a-hexahydro-1H-cyclopenta[c]furan-5-yl]oxy]-2-(2-methoxyphenyl)acetic acid (1.60 g, 5.5 mmol) was dissolved in tetrahydrofuran (15 mL), then borane tetrahydrofuran solution (11 mL, 1 mol/L) was slowly added dropwise to the mixture in an ice bath. The mixture was stirred at room temperature for 4 hours. In an ice bath, methanol (15 mL) was slowly added dropwise to quench the reaction. The reaction solution was concentrated under vacuum, and the residue was purified by silica gel column chromatography [petroleum ether/ethyl acetate (v/v)=2/1] to obtain the product as a colorless oil (0.40 g, 30%).

Step 5 4-[(2R)-2-[[(3aR,5s,6aS)-3,3a,4,5,6,6a-hexahydro-1H-cyclopenta[c]furan-5-yl]oxy]-2-(2-methoxyphenyl)ethoxy]-4-oxo-butanoic acid 2-[[(3aR,5s,6aS)-3,3a,4,5,6,6a-hexahydro-1H-cyclopenta[c]furan-5-yl]oxy]-2-(2-methoxyphenyl)ethanol (0.40 g, 1.0 mmol) was dissolved in tetrahydrofuran (10 mL), then succinic anhydride (0.10 g, 1.0 mmol) was added, the mixture was stirred to dissolve, and then CAL-B lipase (0.03 g) was added. The solution was stirred at room temperature for 20 hours. The resulting solution was filtered with suction and concentrated under vacuum. To the residue was added saturated sodium bicarbonate (20 mL) and then the resulting mixture was stirred for 2 hours. The aqueous phase was washed with ethyl acetate (20 mL×2), and the aqueous phase was collected, then adjusted pH at 2 with 4 N dilute hydrochloric acid. The resulting aqueous phase was extracted with ethyl acetate (30 mL×2), the organic phases were combined, and dried with anhydrous sodium sulfate, then filtered with suction and concentrated under vacuum to obtain the product as a white solid (0.20 g, 40%).

Step 6 (2R)-2-[[(3aR,5s,6aS)-3,3a,4,5,6,6a-hexahydro-1H-cyclopenta[c]furan-5-yl]oxy]-2-(2-methoxyphenyl)ethanol 4-[(2R)-2-[[(3aR,5s,6aS)-3,3a,4,5,6,6a-hexahydro-1H-cyclopenta[c]furan-5-yl]oxy]-2-(2-methoxyphenyl)ethoxy]-4-oxo-butanoic acid (0.20 g, 0.5 mmol) was dissolved in tetrahydrofuran (10 mL), a sodium hydroxide aqueous solution with a mass content of 10% (10 mL) was slowly added dropwise to the system in an ice bath, and after the addition, the mixture was moved to room temperature and stirred for 1 hour. The resulting solution was extracted with ethyl acetate (10 mL×2), the organic phases were combined, and

Step 7 [(2R)-2-[[(3aR,5s,6aS)-3,3a,4,5,6,6a-hexahydro-1H-cyclopenta[c]furan-5-yl]oxy]-2-(2-methoxyphenyl)ethyl]methyl methylsulfonate (2R)-2-[[(3aR,5s,6aS)-3,3a,4,5,6,6a-hexahydro-1H-cyclopenta[c]furan-5-yl]oxy]-2-(2-methoxyphenyl)ethanol (0.10 g, 0.36 mmol) was dissolved in dichloromethane (10 mL), then triethylamine (0.10 mL, 0.70 mmol) was added. To the mixture was slowly added dropwise methanesulfonyl chloride (0.06 mL, 0.72 mmol) in an ice bath, after the addition, the mixture was moved to room temperature and stirred for 5 hours. The resulting solution was filtered under vacuum, the filtrate was diluted with dichloromethane (10 mL), the organic phase was washed with saturated sodium chloride aqueous solution (10 mL×2), and dried over anhydrous sodium sulfate, then filtered with suction and concentrated under vacuum to obtain the product as a colorless oil (0.11 g, 86%).

Step 8 (3aR,5s,6aS)-5-[(1R)-2-bromo-1-(2-methoxyphenyl)ethoxy]-3,3a,4,5,6,6a-hexahydro-1H-cyclopenta[c]furan

[(2R)-2-[[(3aR,5s,6aS)-3,3a,4,5,6,6a-hexahydro-1H-cyclopenta[c]furan-5-yl]oxy]-2-(2-methoxyphenyl)ethyl] methyl methylsulfonate (0.11 g, 0.31 mmol) was dissolved in N-methylpyrrolidone (10 mL), and then lithium bromide (0.20 g, 1.54 mmol) was added, the mixture was heated to 80° C. and stirred for 5 hours. The resulting solution was cooled to room temperature, then water (20 mL) was added, and extracted with ethyl acetate (20 mL) and separated. The organic phase was washed with saturated sodium chloride aqueous solution (20 mL×2), and dried with anhydrous sodium sulfate, then filtered with suction and concentrated under vacuum. The residue was purified by silica gel column chromatography [petroleum ether/ethyl acetate (v/v)=5/1] to obtain the product as a colorless oil (45 mg, 43%).

Step 9 tert-butyl 2-[1-[(2R)-2-[[(3aR,5s,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methylpropanoate Under $N_2$, (3aR,5s,6aS)-5-[(1R)-2-bromo-1-(2-methoxyphenyl)ethoxy]-3,3a,4,5,6,6a-hexahydro-1H-cyclopenta[c]furan (45 mg, 0.13 mmol) and tert-butyl 2-methyl-2-(5-methyl-6-oxazol-2-yl-2,4-dioxo-1H-thieno[2,3-d]pyrimidin-3-yl)propionate (50 mg, 0.13 mmol) were dissolved in anhydrous N-methylpyrrolidone (10 mL), and then potassium carbonate (20 mg, 0.14 mmol) was added, the mixture was heated to 130° C. and stirred for 17 hours. The resulting solution was cooled to room temperature, then water (20 mL) and ethyl acetate (20 mL) were added and separated. The organic phase was washed with saturated sodium chloride aqueous solution (10 mL×2), and dried over anhydrous sodium sulfate, filtered with suction and concentrated under vacuum. The residue was purified by silica gel column chromatography [petroleum ether/ethyl acetate (v/v) =3/1] to obtain the product as a colorless oil (22 mg, 26%).

Step 10 2-[1-[(2R)-2-[[(3aS,5s,6aR)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methylpropionic acid Tert-butyl 2-[1-[(2R)-2-[[(3aR,5s,6aS)-3,3a,4,5,6,6a-hexahydro-1H-cyclopenta[c]furan-5-yl]oxy]-2-(2-methoxyphenyl)ethyl]-5-methyl-6-oxazol-2-yl-2,4-dioxo-thieno[2,3-d]pyrimidin-3-yl]-2-methylpropanoate (22 mg, 0.03 mmol) was dissolved in isopropanol (8 mL), the mixture was cooled to 5° C., and then sulfuric acid (8 mL, 9 mol/L) was added dropwise to the system. After the addition, the mixture was reacted overnight while keeping the temperature. The resulting solution was slowly added to ice water (20 mL), then stirred for 30 minutes, and filtered under vacuum. The filter cake was washed with water (5 mL), then the filter cakes were collected and dried to obtain the product as a white solid (15 mg, 74%).

MS (ESI, pos. ion) m/z: 596.2 $[M+H]^+$.

$^1$H NMR (400 MHz, $CDCl_3$) δ 7.72 (s, 1H), 7.54 (d, J=7.1 Hz, 1H), 7.31 (d, J=7.7 Hz, 1H), 7.25 (s, 1H), 7.04 (t, J=7.5 Hz, 1H), 6.88 (d, J=8.3 Hz, 1H), 5.30-5.24 (m, 1H), 4.19-4.09 (m, 1H), 4.08-3.99 (m, 1H), 3.95-3.91 (m, 1H), 3.90 (s, 3H), 3.58-3.46 (m, 4H), 2.87 (s, 3H), 2.67-2.50 (m, 3H), 2.29-2.20 (m, 1H), 1.89 (s, 3H), 1.85 (s, 3H), 1.43-1.37 (m, 2H).

Biological Activity Test

1. In Vitro Inhibitory Activity Test of Acetyl-CoA Carboxylase:

(1) Test Method

The in vitro inhibitory effects of the compounds on ACC1 or ACC2 were tested by ADP-Glo™ Kinase Analysis Kit from Promega Company. The ADP-Glo™ Kinase Analysis was a luminescent ADP detection analysis, which was used to measure enzyme activity by quantifying the amount of ADP produced during the enzyme reaction. The analysis was performed with two steps: first, after the enzyme reaction, ADP-Glo™ reagent was added to stop the reaction and deplete the remaining ATP; then, a kinase detection reagent was added to simultaneously convert ADP to ATP and the newly synthesized ATP was measured using the luciferase/luciferin reaction. The luminescence can be correlated to the ADP concentration by using the ATP to ADP conversion curve.

The specific steps are as follows:

a. 4.5 μL/well of ACC1/ACC2 working solution (2.22 nM) was added to a 384-well reaction plate (PerkinElmer, 6007290);

b. The compound (10 mM stock solution) was diluted 500 times to 20 μM with 100% DMSO, and diluted in a ratio of 1:3 in a 384 dilution plate (3657, corning). The gradient concentrations of the compound were 20, 6.67, 2.22 0.74, 0.25, 0.082, 0.027, 0.009, 0.003, 0.001, 0 μM;

c. 0.5 μL/well of the compound solution (prepared in step b) was transferred to the 384-well reaction plate (prepared in step a), then plate was centrifuged at 1000 rpm and incubated at 25° C. for 15 minutes;

d. 5 μL/well of substrate mixture solution [ATP (10 mM), Acetyl-CoA (2 mM), $NaHCO_3$ (1000 mM)] was transferred to the 384-well reaction plate, then plate was centrifuged at 1000 rpm and incubated at 25° C. for 30 minutes. The compound final gradient concentrations in the reaction system were 1000, 333.3, 111.1, 37.04, 12.35, 4.12, 1.37, 0.46, 0.15, 0.05, 0 nM. The final concentration of DMSO was 5%; the final concentration of ACC1/ACC2 was 1 nM;
e. 10 μL/well of ADP-Glo solution was transferred to the 384-well reaction plate, then the plate was centrifuged at 1000 rpm and incubated at 25° C. for 40 minutes;
f. 20 μL/well of kinase detection reagent was transferred to the 384-well reaction plate, then the plate was centrifuged at 1000 rpm and incubated at 25° C. for 40 minutes;
g. Relative luminescence unit (RLU) was read on an Envision multifunction plate reader. The signal intensity was used to characterize the activity of ACC1/ACC2 kinase.

The ACC1/ACC2 working solution, substrate mixture solution, ADP-Glo solution and kinase detection reagent used in the test were all prepared by using 1×kinase reaction buffer [hydroxyethylpiperazineethanesulfonic acid (HEPES, 50 mM), $MgCl_2$ (2 mM), lauryl polyglycol ether(BRIJ-35, 0.01%), potassium citrate (2 mM), bovine serum albumin (BSA, 50 μg/mL), dithiothreitol (DTT, 2 mM)].

The average values of each concentration and the data of the positive and negative controls were calculated, as well as the standard deviation. The percentage of inhibition was calculated by the formula: 100×(average negative control−compound)/(average negative control−average positive control). The $IC_{50}$ for each compound was calculated by fitting the data with a nonlinear regression equation: Y=Bottom+(Top−Bottom)/(1+10^((Log $IC_{50}$−X)×HillSlope)), wherein X is the log of compound concentration and Y is the percentage of inhibition.

(2) Results

Results of in vitro inhibitory activity of the compounds of the present invention on ACC1 and ACC2 are shown in table 2.

TABLE 2

In vitro inhibitory activity of the compounds on ACC1 and ACC2

| compounds | ACC1 $IC_{50}$ (nM) | ACC2 $IC_{50}$ (nM) |
|---|---|---|
| A13 | 1.76 | 4.24 |
| Example 1 | 1.42 | 3.65 |
| Example 2 | 1.09 | 3.82 |
| Example 3 | 0.23 | 2.43 |

The experimental results show that the compounds of the present invention have good inhibitory effects on ACC1 and ACC2.

Pharmacokinetic Test

1. Organizational Distribution

C57BL/6 mice were used as the test animals, the LC-MS/MS method was used to determine the drug concentration in plasma and liver at different times after the mice were administered intragastrically the compounds of Examples 1 to 3 and A13. Pharmacokinetic properties of the compounds of the present invention in mice were studied.

(1) Test Method

The prescriptions of A13, Example 1 and Example 2 were: 5% DMSO+5% Kolliphor HS15+90% Saline The prescription of Example 3 was: 10% DMSO+10% Kolliphor HS15+80% Saline Healthy adult C57BL/6 male mice, purchased from Hunan Slack Jingda Experimental Animal Co., Ltd., with an animal weight of 18-24 g, were administered intragastrically at a dosage of 5 ml/kg and a volume of 10 ml/kg.

(2) Sample Collection

Bloods were collected from the orbit at different time points, and the whole blood samples were placed in an anticoagulation tube containing EDTA-K2; the plasma was separated by centrifugation (centrifugation conditions: 12000 rpm, 2 min) and the upper plasma sample was collected and placed into a sample tube.

Animals were dissected and collected livers at different time points, a certain mass of liver tissue was weighed, 5 times the volume (m/V) of methanol solution was added to the homogenization tube, then homogenized at 60 hz for 2 minutes and centrifuged at 4° C. for 2 minutes, the supernatant was taken to obtain the liver homogenate.

LC-MS/MS was used to analyze the content of the test compounds in the plasma and liver of the mice after the compounds were administered intragastrically.

(3) Results

TABLE 3

Contents and partition ratios of the compounds of the present invention in the liver/plasma at different time points

| | | Average tissue concentrations (liver) | | | Partition ratios of liver and plasma | | |
|---|---|---|---|---|---|---|---|
| | | 0.5 h | 1 h | 2 h | | | |
| compounds | tissue | ng/g | ng/g | ng/g | 0.5 h | 1 h | 2 h |
| A13 | liver | 61500 | 33300 | 14000 | 86 | 130 | 170 |
| | plasma | 717 | 249 | 82.8 | | | |
| Example 1 | liver | 75000 | 48300 | 35500 | 190 | 140 | 600 |
| | plasma | 391 | 336 | 59.1 | | | |
| Example 2 | liver | 70400 | 40600 | 16900 | 190 | 120 | 180 |
| | plasma | 373 | 351 | 96.4 | | | |
| Example 3 | liver | 75500 | — | 26500 | 122 | — | 104 |
| | plasma | 669 | — | 253 | | | |

"—" means not tested;

Experimental results show that after oral administration, the compounds of the present invention have a higher drug concentration than A13 in the liver of mice target tissue, a higher ratio of liver and plasma, a longer action time, and obvious advantages.

2. Liver Microsome Stability Test
2.1 Experimental Drugs and Materials

Example 1, A13

Male CD-1 mouse liver microsomes, purchased from BD Gentest.

2.2 Solution Preparation

Preparation of stock solution: a certain amount of test compound of A13 and Example 1 were weighed to prepare a stock solution with a concentration of 10 mM with DMSO, and stored in a refrigerator at −20° C.

Preparation of 0.1M potassium phosphate buffer solution (pH=7.4): 0.1 M potassium dihydrogen phosphate solution: a certain amount of potassium dihydrogen phosphate was weighed, and dissolved ultrasonically with ultrapure water, and then ultrapure water was added to make the concentration of potassium dihydrogen phosphate solution 0.1 M.

0.1 M dipotassium phosphate solution: a certain amount of dipotassium phosphate was weighed, and dissolved ultrasonically with ultrapure water, and then ultrapure water was added to make the concentration of dipotassium phosphate solution 0.1 M.

0.1 M potassium phosphate buffer (pH=7.4): 0.1 M potassium dihydrogen phosphate solution was slowly added to 0.1 M dipotassium phosphate solution, and the addition was stopped when the pH was 7.4.

Preparation of NADPH solution: a certain amount of NADPH to be tested was weighed and prepared a solution with a concentration of 6 mM with 0.1 M potassium phosphate buffer (5 mg of NADPH was weighed and added to 1 mL of potassium phosphate buffer, the concentration was equivalent to 6 mM).

Preparation of compound dosing solution: 100 μM dosing solution: 5 μL of 10 mM stock solution was added to 495 μL of acetonitrile:water (1:1); 30 μM dosing solution: 60 μL of 100 μM dosing solution was added to 140 μL of 0.1 M potassium phosphate buffer; 1.5 μM dosing solution: 25 μL of 30 μM dosing solution and 18.8 μL (20 mg/mL) of liver microsomes were added to 456.2 μL of 0.1 M potassium phosphate buffer, one for each species.

Preparation of internal standard solution: internal standard stock solution was taken and diluted with acetonitrile to a concentration of 100 nM for later use.

2.3 Experimental Steps

μ30 μL of 1.5 μM dosing solution of the compound was added to a 96-well plate, 150 μL or 200 μL of acetonitrile internal standard was added immediately to the plate, then 15 μL of NADPH solution (6 mM) was added to the plate, the mixture was mixed well and placed in a 4° C. refrigerator as the initial 0 point sample, each drug was made two holes in parallel.

30 μL of 1.5 μM dosing solution was added to positions set at different time points in the 96-well plate, each drug was made two holes in parallel, and the pleat was preheated at 37° C. for 10 min.

After pre-incubation, 15 μL of NADPH solution (6 mM) was added to the well set at the time point of 60 min, at the time point of NCF60, 15 μL of potassium phosphate buffer salt solution was added at the same time to start the reaction and start timing. Then after 40 min, 15 μL of NADPH solution was added to the well set at 20 min. After 20 min, the incubation was over. 150 or 200 μL of acetonitrile internal standard was added to the positions set at all time points. The plate was centrifuged at 4000 rpm for 5 min, 50 μL supernatant was taken out and diluted with 150 μL water for sample analysis.

2.4 Data Processing

The initial 0 point was used as 100%, the relative content of the drug at each time point was calculated. GraphPad Prism5 software was used to plot the "relative content of the drug" versus "incubation time" to calculate the half-life of the drug and calculate the intrinsic clearance rate.

The calculation formula is as follows:

| species | Liver microsomal protein per gram of liver (mg) | Liver weight per kilogram of body weight (g) | Amplification factor [a] | Liver blood flow rate (ml/min/kg) |
|---|---|---|---|---|
| Mouse | 45 | 87.5 | 3937.5 | 90 |

[a] Amplification factor = (liver microsomal protein per gram of liver) × (liver weight per kilogram of body weight)
Intrinsic clearance rate = $(0.693/T_{1/2}) \times (1/(\text{liver microsome concentration } (0.5 \text{ mg/ml}))) \times$ magnification factor
Hepatic clearance rate $(Cl_{Hep}) = (0.693/T_{1/2}) \times 1/(\text{liver microsome concentration } (0.5 \text{ mg/mL})) \times$ amplification factor;
In vivo clearance rate $(Cl_{in\ vivo})$ = hepatic clearance rate × liver blood flow rate/(hepatic clearance rate + liver blood flow rate);
Extraction rate (ER) = body clearance rate/liver blood flow rate.

2.5 Results

TABLE 4

Results of stability test of liver microsomes of the compounds of the present invention

| | | | | | | Mouse | |
|---|---|---|---|---|---|---|---|
| | | | | | | Remaining (%) | |
| compounds | Conc. (μM) | $T_{1/2}$ (min) | $Cl_{Hep}$ (mL/min/kg) | $Cl_{in\ vivo}$ (mL/min/kg) | ER | (T = 60 min) | (NCF = 60 min) |
| A13 | 1 | 89.56 | 60.9 | 36.3 | 0.4 | 63.4 | 81.0 |
| Example 1 | 1 | 145 | 38.0 | 9.6 | 0.1 | 71.9 | 90.6 |

Slow Metabolism (ER < 0.3), Medium Metabolism (0.3 < ER < 0.7), Fast Metabolism (ER > 0.7)

The experimental results show that the compounds provided herein are more stable in liver microsomes of the mice and have a slower metabolism, and are more advantageous than A13.

Note: The structure of the control substance A13 is as follows, prepared according to WO2018133858

A13

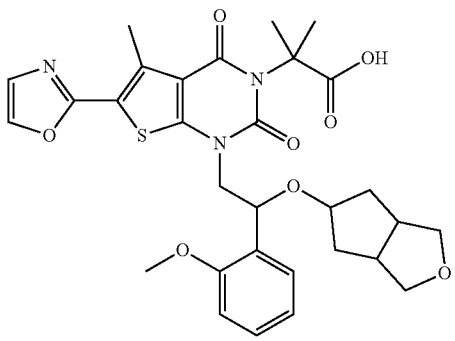

Finally, it should be noted that there are other ways to practice the invention. Accordingly, embodiments of the present invention are to be described as examples, but the present invention is not limited to the contents described, further modifications may be made within the scope of the present invention or the equivalents added in the claims. All publications or patents cited herein are incorporated by reference herein.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a pharmaceutically acceptable salt thereof,

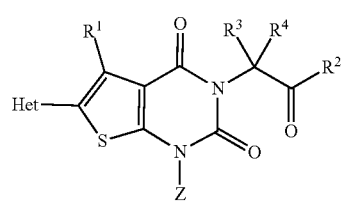

(I)

wherein:
Z has the following structures:

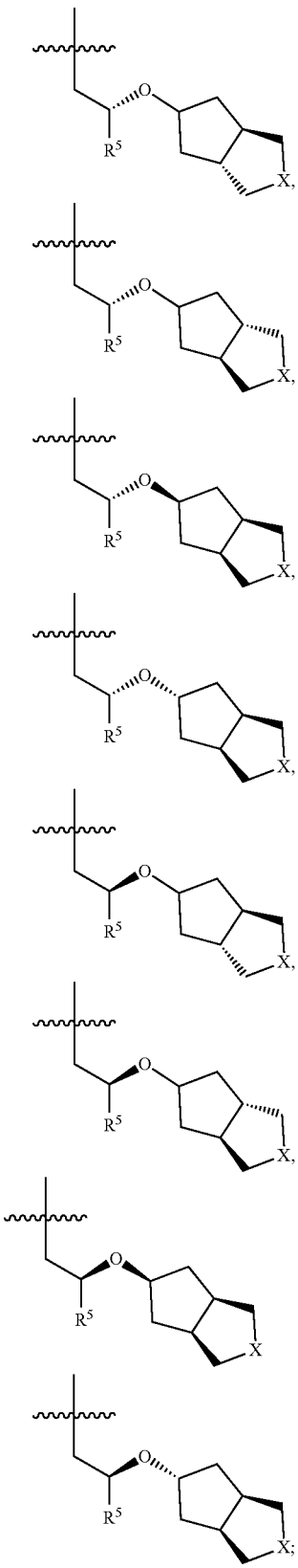

Het is 3-10 membered heterocyclyl or 5-10 membered heteroaryl, the 3-10 membered heterocyclyl and 5-10 membered heteroaryl can be optionally substituted by 1, 2, 3 or 4 substituents independently selected from H, D, oxo (=O), F, Cl, Br, I, hydroxyl, amino, nitro, cyano, $C_{1-6}$ alkyl, $C_{1-6}$ alkoxy, $C_{1-6}$ haloalkyl and carboxyl;

$R^1$ is H, D, F, Cl, Br, I, hydroxyl, amino, nitro, cyano, $C_{1-6}$ alkyl, $C_{1-6}$ alkoxy or $C_{1-6}$ haloalkyl;

$R^2$ is —OR or —NR$^a$R$^b$, each $R^3$ and $R^4$ is independently H, D, $C_{1-6}$ alkyl, $C_{1-6}$ hydroxyalkyl or $C_{1-6}$ haloalkyl;

each $R^5$ is independently $C_{6-10}$ aryl or 5-10 membered heteroaryl, the $C_{6-10}$ aryl and 5-10 membered heteroaryl can be optionally substituted by 1, 2 or 3 $R^6$; wherein, each $R^6$ is independently H, D, F, Cl, Br, I, hydroxyl, amino, nitro, cyano, $C_{1-6}$ alkyl, $C_{1-6}$ alkoxy, $C_{1-6}$ haloalkyl, $C_{1-6}$ haloalkoxy, $C_{1-6}$ cyanoalkyl or $C_{1-6}$ hydroxyalkyl;

each X is independently O or NR$^7$;

each $R^7$ is independently H, D, F, Cl, Br, I, hydroxyl, amino, nitro, cyano, —C(=O)OH, —SO$_2$R$^c$, $C_{1-6}$ alkyl, $C_{3-6}$ cycloalkyl, $C_{1-6}$ alkoxy, $C_{1-6}$ haloalkoxy, $C_{1-6}$ alkylamino, $C_{1-6}$ haloalkyl, $C_{1-6}$ cyanoalkyl or $C_{1-6}$ hydroxyalkyl;

each R, R$^a$, R$^b$ and R$^c$ is independently H, D, $C_{1-6}$ alkyl, $C_{1-6}$ alkoxy, $C_{3-6}$ cycloalkyl or $C_{1-6}$ haloalkyl;

or, R$^a$ and R$^b$, together with the N atom to which they are attached, form 4-6 membered heterocyclyl, and the 4-6 membered heterocyclyl can be optionally substituted by 1, 2, 3 or 4 substituents independently selected from oxo (=O), D, F, Cl, Br, I, hydroxy, amino, nitro, cyano, $C_{1-3}$ alkyl, $C_{1-3}$ alkoxy and $C_{1-3}$ haloalkyl.

2. The compound of claim 1, wherein the X is O, NH or N—SO$_2$R$^c$; R$^c$ is H, D, methyl, ethyl, isopropyl, methoxy or ethoxy.

3. The compound of claim 1, wherein the Het is

[chemical structures]

wherein, the Het can be optionally substituted by 1, 2, 3 or 4 substituents independently selected from H, D, oxo (=O), F, Cl, Br, I, hydroxyl, amino, nitro, cyano, methyl, ethyl, isopropyl, methoxy, ethoxy, isopropyloxy, trifluoromethyl, difluoromethyl and carboxyl.

4. The compound of claim 1, wherein the $R^1$ is H, D, F, Cl, Br, I, hydroxyl, amino, nitro, cyano, methyl, ethyl, methoxy, ethoxy, isopropyloxy or trifluoromethyl;

$R^2$ is —OR or —NR$^a$R$^b$;

each R, R$^a$ and R$^b$ is independently H, D, methyl, ethyl, methoxy, ethoxy, cyclopropyl, cyclobutyl, cyclopentyl or cyclohexyl; or, R$^a$ and R$^b$, together with the N atom to which they are attached, form 4-6 membered heterocyclyl, and the 4-6 membered heterocyclyl is selected from:

[chemical structures]

-continued

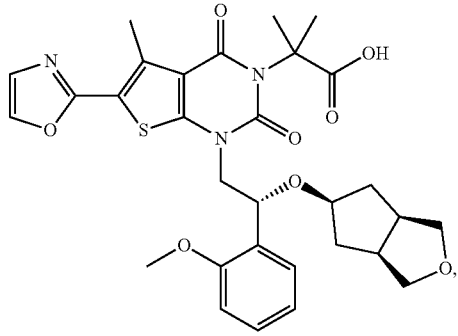

the 4-6 membered heterocyclyl can be optionally substituted by 1, 2, 3 or 4 substituents independently selected from oxo (=O), D, F, Cl, Br, I, hydroxyl, amino, nitro, cyano, methyl, ethyl, isopropyl, methoxy, ethoxy, trifluoromethyl and difluoromethyl;

each $R^3$ and $R^4$ is independently H, D, methyl, ethyl, n-propyl, hydroxymethyl, difluoromethyl, trifluoromethyl or 2-hydroxyethyl;

each $R^5$ is independently phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl or pyridazinyl; wherein the phenyl, naphthyl, 1,2,3,4-tetrahydronaphthyl, imidazolyl, pyrazolyl, furyl, thienyl, oxazolyl, oxadiazolyl, thiazolyl, thiadiazolyl, triazolyl, tetrazolyl, pyridyl, pyrimidinyl, pyranyl and pyridazinyl can be optionally substituted by 1, 2 or 3 $R^6$; wherein each $R^6$ is independently H, D, F, Cl, Br, I, hydroxyl, amino, nitro, cyano, methyl, ethyl, n-propyl, isopropyl, methoxy, ethoxy, trifluoromethyl, difluoromethyl, trifluoromethoxy, difluoromethoxy, hydroxymethyl or 2-hydroxyethyl.

5. The compound of claim 1 having one of the following structures:

(1)
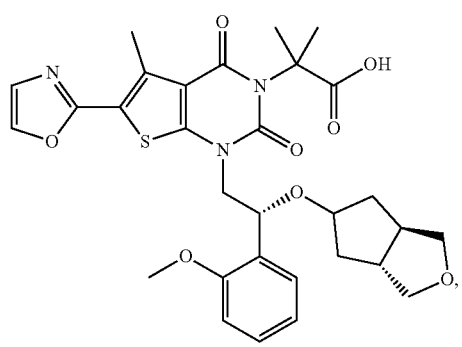

(2)
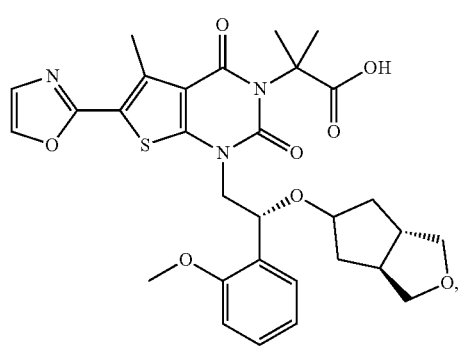

(3)
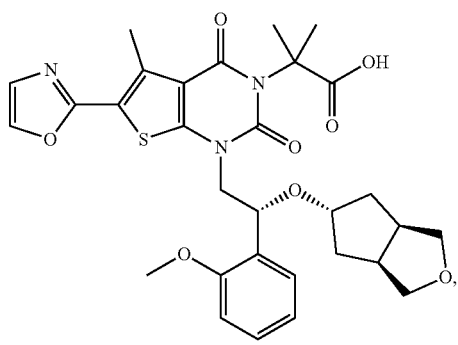

(4)
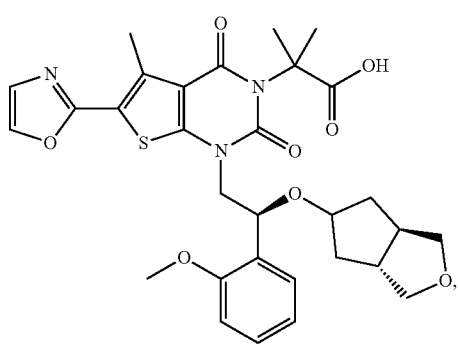

(5)
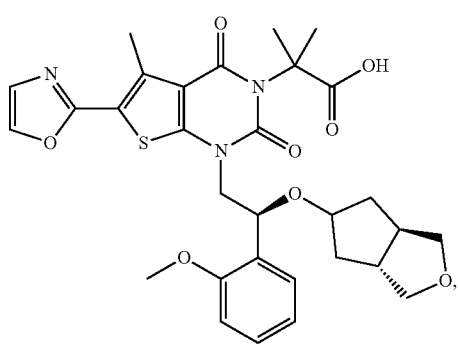

(6)
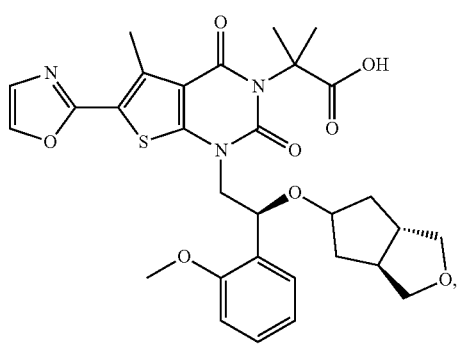

(7)

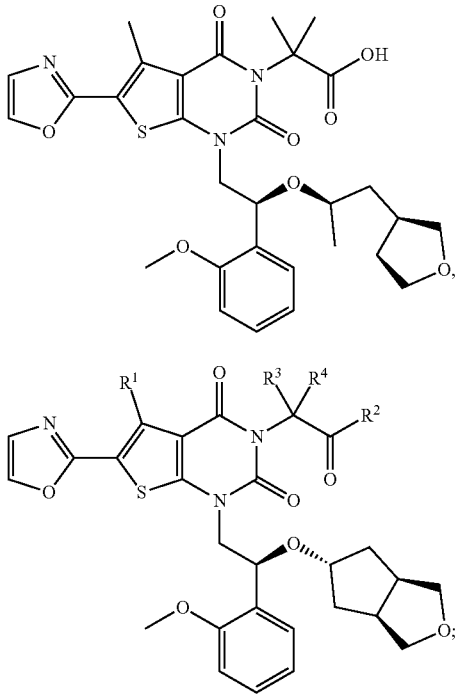

(8)

or a pharmaceutically acceptable salt thereof.

6. A pharmaceutical composition comprising the compound of claim 1.

7. The composition of claim 6, further comprising a pharmaceutically acceptable carrier, an excipient, a diluent, an adjuvant, a vehicle or any combination thereof.

8. A method of treating diseases regulated by Acetyl-CoA carboxylase in a patient comprising administering to the patient a therapeutically effective amount of the compound of claim 1.

9. The method of claim 8, wherein the diseases regulated by Acetyl-CoA carboxylase are metabolic disorders.

10. The method of claim 8, wherein the diseases regulated by ACC Acetyl-CoA carboxylase comprise metabolic disorders, the metabolic disorders comprise insulin resistance, obesity, dyslipidemia, metabolic syndrome, type II diabetes, non-alcoholic fatty liver, non-alcoholic steatohepatitis, liver steatosis, bullous steatosis, advanced fibrosis or cirrhosis.

11. A method of treating diseases regulated by Acetyl-CoA carboxylase in a patient comprising administering to the patient a therapeutically effective amount of the pharmaceutical composition of claim 6.

12. The method of claim 11, wherein the diseases regulated by Acetyl-CoA carboxylase are metabolic disorders.

13. The method of claim 11, wherein the diseases regulated by ACC Acetyl-CoA carboxylase comprise metabolic disorders, the metabolic disorders comprise insulin resistance, obesity, dyslipidemia, metabolic syndrome, type II diabetes, non-alcoholic fatty liver, non-alcoholic steatohepatitis, liver steatosis, bullous steatosis, advanced fibrosis or cirrhosis.

* * * * *